US008693802B2

(12) United States Patent
Watanabe et al.

(10) Patent No.: US 8,693,802 B2
(45) Date of Patent: Apr. 8, 2014

(54) FLUOROSCOPY APPARATUS, FLUOROSCOPY SYSTEM, AND FLUORESCENCE-IMAGE PROCESSING METHOD

(71) Applicant: Olympus Corporation, Tokyo (JP)

(72) Inventors: Toshiaki Watanabe, Tokyo (JP); Yasushige Ishihara, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/834,395

(22) Filed: Mar. 15, 2013

(65) Prior Publication Data

US 2013/0200273 A1     Aug. 8, 2013

Related U.S. Application Data

(60) Division of application No. 13/235,886, filed on Sep. 19, 2011, now Pat. No. 8,472,749, which is a continuation of application No. PCT/JP2010/054510, filed on Mar. 17, 2010.

(30) Foreign Application Priority Data

Mar. 24, 2009   (JP) ................................. 2009-072852

(51) Int. Cl.
    *G06K 9/00*     (2006.01)
(52) U.S. Cl.
    USPC ............ 382/274; 382/128; 382/162; 382/166
(58) Field of Classification Search
    USPC ......................... 382/128–134, 162–167, 274
    See application file for complete search history.

(56) References Cited

U.S. PATENT DOCUMENTS

| 7,260,248 B2 * | 8/2007 | Kaufman et al. ............. 382/128 |
| 8,031,938 B2 * | 10/2011 | Edge ............................. 382/167 |
| 2003/0144585 A1 | 7/2003 | Kaufman et al. |
| 2004/0240716 A1 * | 12/2004 | de Josselin de Jong et al. ............................ 382/128 |

(Continued)

FOREIGN PATENT DOCUMENTS

| JP | 62-247232 | 10/1987 |
| JP | 2001-137173 | 5/2001 |
| JP | 2001-169999 A | 6/2001 |
| JP | 2005-185452 A | 7/2005 |
| JP | 2008-183349 A | 8/2008 |

OTHER PUBLICATIONS

International Search Report dated May 11, 2010 issued in corresponding International Application No. PCT/JP2010/054510.

(Continued)

*Primary Examiner* — Wesley Tucker
(74) *Attorney, Agent, or Firm* — Scully, Scott, Murphy & Presser, P.C.

(57) ABSTRACT

A fluoroscopy apparatus including: an illumination unit having a light source radiating illumination light and excitation light onto an observation target, a fluorescence-imaging unit acquiring a fluorescence image by imaging fluorescence generated at the observation target by the excitation light, a white-light-imaging unit acquiring a reference image by imaging light returning from the observation target by the illumination light, and an image-correction unit obtaining a correction fluorescence image by raising the luminance value of the fluorescence image to the power of a reciprocal of a first and second exponent obtained by a power approximation of a distance characteristic of luminance versus observation distance, for the fluorescence image, and that obtains a corrected fluorescence image by dividing the correction fluorescence image by the correction reference image.

20 Claims, 26 Drawing Sheets

(56) References Cited

U.S. PATENT DOCUMENTS

| | | | |
|---|---|---|---|
| 2008/0247624 A1* | 10/2008 | Scholz | 382/131 |
| 2008/0255426 A1 | 10/2008 | Iketani | |
| 2010/0292543 A1* | 11/2010 | Levitt et al. | 600/300 |
| 2013/0028501 A1* | 1/2013 | Ishihara | 382/132 |

OTHER PUBLICATIONS

Notice of Allowance and Issue Fee Due dated Feb. 28, 2013 issued in corresponding U.S. Appl. No. 13/235,886.

* cited by examiner

D0 IMAGE

D1 IMAGE

D2 IMAGE

DO IMAGE

D1 IMAGE

D2 IMAGE

FIG. 7

| CORRECTED FLUORESCENCE IMAGE LUMINANCE VALUE | FLUORESCENCE CONCENTRATION (nM) |
|---|---|
| 0 | 0 |
| 1 | 1 |
| ⋮ | ⋮ |
| 4095 | 1000 |

87

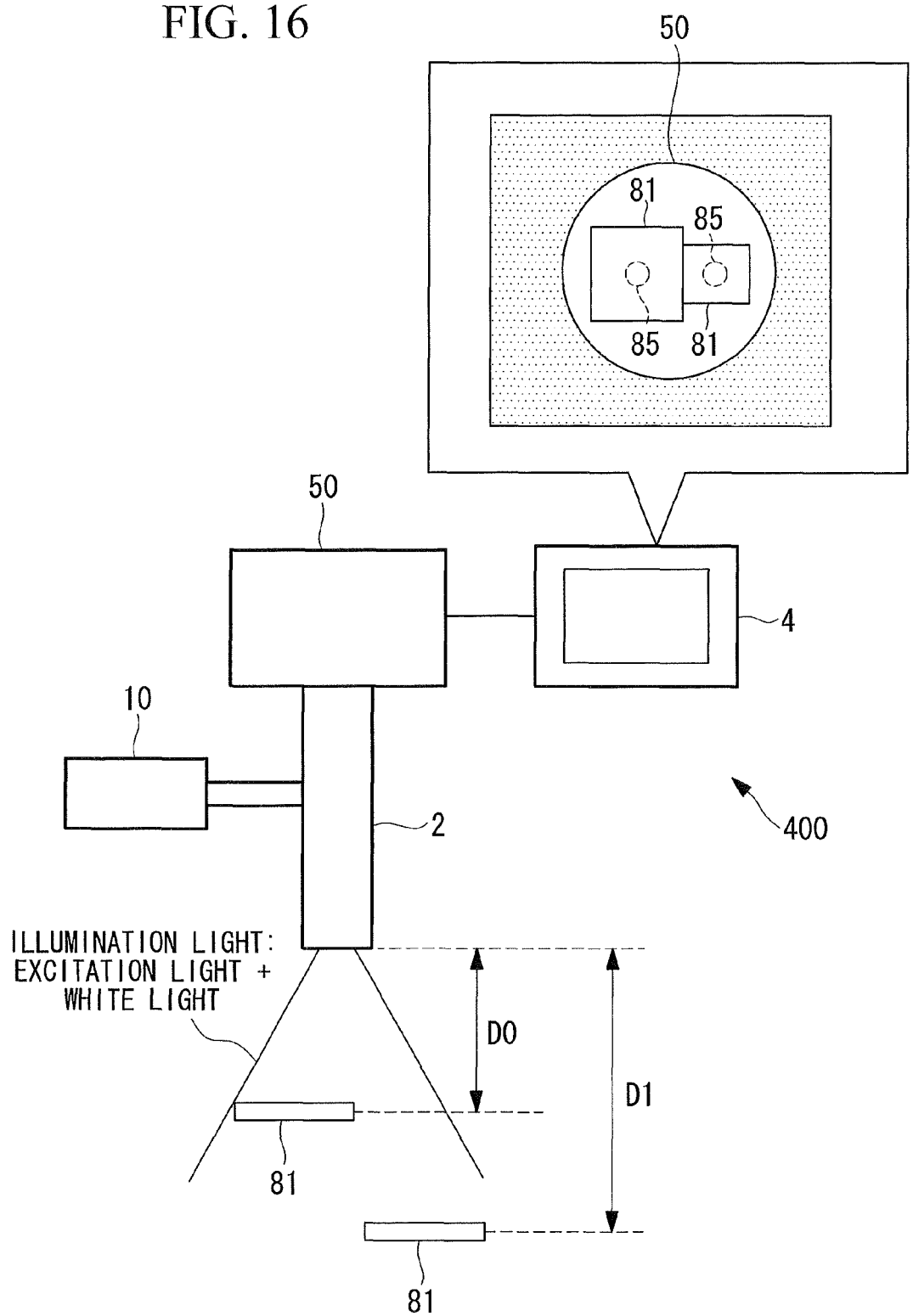

FIG. 21

| CORRECTION FACTOR a | STANDARD DEVIATION $\sigma$ OF FL/RL$^a$ IN REGION OF INTEREST |
|---|---|
| 1 (NO CORRECTION) | 1 |
| 0.95 | 0.95 |
| ⋮ | ⋮ |
| 0.5 | 0.5 |

FLUOROSCOPY APPARATUS, FLUOROSCOPY SYSTEM, AND FLUORESCENCE-IMAGE PROCESSING METHOD

CROSS REFERENCE TO RELATED APPLICATIONS

This application is a divisional application of U.S. Ser. No. 13/235,886 filed Sep. 19, 2011, which is a continuation of International Application PCT/JP2010/054510, with an international filing date of Mar. 17, 2010, each of which are incorporated by reference herein in their entirety. This application claims the benefit of Japanese Patent Application No. 2009-072852, the content of which is incorporated herein by reference.

TECHNICAL FIELD

The present invention relates to a fluoroscopy apparatus, a fluoroscopy system, and a fluorescence-image processing method.

BACKGROUND ART

In the related art, there is a known fluoroscopy apparatus that is capable of obtaining a high-luminance fluorescence image of a lesion by radiating excitation light, which excites fluorescent dye to generate agent-fluorescence, onto an observation target site, to which a fluorescent dye that specifically accumulates at a lesion, such as cancer cells, is administered, and by capturing the agent-fluorescence generated (for example, see Patent Literature 1).

In the fluoroscopy apparatus described in Patent Literature 1, since the intensity of the excitation light radiated onto an observation target site varies depending on distance, in order to correct the influence due to the distance, arithmetic processing in which a fluorescence image of the observation target site is divided by a reflected-light image of the same observation target site is performed.

CITATION LIST

Patent Literature

{PTL 1} Japanese Unexamined Patent Application, Publication No. Sho 62-247232.

SUMMARY

The present invention employs the following solutions.

A first aspect of the present invention is a fluoroscopy apparatus including, an illumination portion having a light source that radiates illumination light and excitation light onto a subject, a fluorescence-imaging unit that acquires a fluorescence image by imaging fluorescence generated at the subject by the radiation of the excitation light from the illumination portion, a return-light imaging unit that acquires a reference image by imaging return light returning from the subject by the radiation of the illumination light from the illumination portion, and an image-correction unit that corrects the fluorescence image acquired by the fluorescence-imaging unit by using the reference image acquired by the return-light imaging unit, wherein in the image-correction unit, a correction fluorescence image is obtained by raising a luminance value of the fluorescence image to the power of the reciprocal of a first exponent that is obtained by a power approximation of a characteristic of luminance versus distance from the illumination portion to the subject, for the fluorescence image acquired by the fluorescence-imaging unit when the excitation light of a prescribed intensity is radiated towards the subject; a correction reference image is obtained by raising a luminance value of the reference image to the power of the reciprocal of a second exponent that is obtained by a power approximation of a characteristic of luminance versus distance from the illumination portion to the subject, for the reference image obtained by the return-light imaging unit when the illumination light of a prescribed intensity is radiated towards the subject; and a corrected fluorescence image is obtained by dividing the correction fluorescence image by the correction reference image.

According to this aspect, by radiating the excitation light emitted from the illumination portion onto the subject, the fluorescence generated at the subject is imaged by the fluorescence-imaging unit imaging unit and a fluorescence image is acquired, and by radiating the illumination light emitted from the illumination portion together with the excitation light onto the subject, the return light thereof is imaged by the return-light imaging unit and a reference image is acquired.

In this case, the fluorescence image acquired by the fluorescence-imaging unit contains information related to the fluorescence that is raised to the power of the distance from the illumination portion to the subject, and the reference image acquired by the return-light imaging unit contains information related to the illumination light that is raised to the power of the distance from the illumination portion to the subject. In addition, because the fluorescence and return-light characteristics differ if they are influenced by internal scattering, surface reflection, or the like, the characteristic of the luminance of the fluorescence image on the distance from the illumination portion to the subject differs from the characteristic of the luminance of the reference image on the distance from the illumination portion to the subject.

According to the fluoroscopy apparatus of the present invention, in the image-correction unit, by raising the luminance value of the fluorescence image to the power of the reciprocal of the first exponent obtained by a power approximation of the characteristic of the luminance versus distance from the illumination portion to the subject, for the fluorescence image, it is possible to obtain the correction fluorescence image having a substantially constant luminance relative to variations in the distance. In addition, by raising the luminance value of the reference image to the power of the reciprocal of the second exponent obtained by a power approximation of the characteristic of the luminance of versus distance from the illumination portion to the subject, for the reference image, it is possible to obtain the correction reference image having a substantially constant luminance relative to the variations of the distance. Therefore, by dividing the correction fluorescence image by the correction reference image, it is possible to obtain a corrected fluorescence image having quantitativeness, in which the dependencies of the fluorescence image and the reference image on distance are cancelled and in which correction is achieved with high accuracy, allowing a lesion to be diagnosed accurately.

In this aspect, the image-correction unit may further raise the luminance value of the corrected fluorescence image to the power of the first exponent.

Configuring in this way, it is possible to reduce the dependency on the distance by the image-correction unit, while maintaining a direct-proportionality relationship between the luminance value of the corrected fluorescence image and the amount of the fluorescent agent present in the subject (i.e., the concentration of fluorescent agent).

A second aspect of the present invention is a fluoroscopy apparatus comprising, an illumination portion having a light source that radiates illumination light and excitation light onto a subject, a fluorescence-imaging unit that acquires a fluorescence image by imaging fluorescence generated at the subject by the radiation of the excitation light from the illumination portion, a return-light imaging unit that acquires a reference image by imaging return light returning from the subject by the radiation of the illumination light from the illumination portion, and an image-correction unit that corrects the fluorescence image acquired by the fluorescence-imaging unit by using the reference image acquired by the return-light imaging unit, wherein in the image-correction unit, a first exponent is obtained by a power approximation of a characteristic of luminance versus distance from the illumination portion to the subject, for the fluorescence image acquired by the fluorescence-imaging unit when the excitation light of a prescribed luminance is radiated towards the subject; a second exponent is obtained by a power approximation of a characteristic of luminance versus distance from the illumination portion to the subject, for a reference image acquired by a return-light imaging unit when the illumination light of a prescribed intensity is radiated towards the subject; a correction reference image is obtained by raising the luminance value of the reference image to the power of a third exponent that is obtained by dividing the first exponent by the second exponent; a correction fluorescence image is obtained by dividing the fluorescence image by the correction reference image, or by raising the luminance value of the fluorescence image to the power of a fourth exponent that is obtained by dividing the second exponent by the first exponent; and a corrected fluorescence image is obtained by dividing the correction fluorescence image by the reference image.

According to this aspect, in the image-correction unit, it is sufficient to perform the power computation only once to correct the influence of the distance with high precision, and it is possible to obtain the corrected fluorescence image in which the luminance value and the amount of the fluorescent agent present have a direct-proportionality relationship.

A third aspect of the present invention is a fluoroscopy apparatus comprising, an illumination portion having a light source that radiates illumination light and excitation light onto a subject, a fluorescence-imaging unit that acquires a fluorescence image by imaging fluorescence generated at the subject by the radiation of the excitation light from the illumination portion, a return-light imaging unit that acquires a reference image by imaging return light returning from the subject by the radiation of the illumination light from the illumination portion, and an image-correction unit that corrects the fluorescence image acquired by the fluorescence-imaging unit by using the reference image acquired by the return-light imaging unit, wherein the image-correction unit obtains a correction fluorescence image by raising a luminance value of the fluorescence image to the power of the first correction factor that is obtained such that ratios of a luminance of the fluorescence image, in which the luminance value of the fluorescence image has been raised to the power of a first correction factor, to a luminance of the reference image match each other at a plurality of different distances, and obtains a corrected fluorescence image by dividing the correction fluorescence image by the reference image.

According to this aspect, only the ratios of the intensities of the luminance of the fluorescence image and of the reference light image at a plurality of different distances need to be obtained, and it is not necessary to obtain the distance information. In addition, because the distance characteristic is not subjected to a power approximation, it is possible to decide the first correction factor with a simple computation.

A fourth aspect of the present invention is a fluoroscopy apparatus comprising, an illumination portion having a light source that radiates illumination light and excitation light onto a subject, a fluorescence-imaging unit that acquires a fluorescence image by imaging fluorescence generated at the subject by the radiation of the excitation light from the illumination portion, a return-light imaging unit that acquires a reference image by imaging return light returning from the subject by the radiation of the illumination light from the illumination portion, and an image-correction unit that corrects the fluorescence image acquired by the fluorescence-imaging unit by using the reference image acquired by the return-light imaging unit, wherein the image-correction unit obtains the correction reference image by raising a luminance value of the reference image to the power of the second correction factor that is obtained such that ratios of a luminance of the fluorescence image to a luminance of the reference image, in which the luminance value of the reference image has been raised to the power of a second correction factor, match each other at a plurality of different distances, and obtains a corrected fluorescence image by dividing the fluorescence image by the correction reference image.

According to this aspect, by deciding only the second correction factor from the luminance information of the fluorescence image and the reference image at a plurality of different distances, it is possible to easily obtain the corrected fluorescence image having high quantitativeness, in which the distance dependencies of the fluorescence image and the reference image are reduced.

A fifth aspect of the present invention is a fluoroscopy apparatus comprising, an illumination portion having a light source that radiates illumination light and excitation light onto a subject, a fluorescence-imaging unit that acquires a fluorescence image by imaging fluorescence generated at the subject by the radiation of the excitation light from the illumination portion, a return-light imaging unit that acquires a reference image by imaging return light returning from the subject by the radiation of the illumination light from the illumination portion, and an image-correction unit that corrects the fluorescence image acquired by the fluorescence-imaging unit by using the reference image acquired by the return-light imaging unit, wherein the image-correction unit obtains a correction fluorescence image by raising a luminance value of the fluorescence image to the power of the first correction factor that is obtained such that ratios of a luminance of the fluorescence image, in which the luminance value of the fluorescence image has been raised to the power of a first correction factor, to a luminance of the reference image, in which the luminance value of the reference image has been raised to the power of a second correction factor, match each other at a plurality of different distances, obtains the correction reference image by raising the luminance value of the reference image to the power of the second correction factor, and obtains a corrected fluorescence image by dividing the correction fluorescence image by the correction reference image.

According to this aspect, by deciding only two correction factors from the luminance information of the fluorescence image and the reference image at a plurality of different distances, it is possible to easily obtain a corrected fluorescence image having high quantitativeness in which the distance dependencies of the fluorescence image and the reference image are reduced.

In the above-described aspect, an image-acquisition condition adjusting portion that adjusts an image acquisition condition on the basis of the luminance value of the fluorescence image acquired by the fluorescence-imaging unit, may be provided, wherein the image-correction unit may normalize the luminance of the fluorescence image by the image acquisition condition.

Configuring in this way, it is possible to obtain a fluorescence image having suitable brightness with the image-acquisition condition adjusting portion regardless of the luminance of the fluorescence generated at the subject. In this case, by normalizing the luminance of the fluorescence image by the image acquisition condition with the image-correction unit, it is possible to standardize the luminance value of the fluorescence image even when the image acquisition condition of the image-acquisition condition adjusting portion is changed.

In the above-described aspect, the image-acquisition condition adjusting portion may adjust exposure time of the fluorescence-imaging unit, and the image-correction unit may divide the luminance value of the fluorescence image by the exposure time.

Configuring in this way, it is possible to adjust the brightness of the fluorescence image by using the image-acquisition condition adjusting portion by changing the exposure time of the fluorescence-imaging unit. In addition, even if the exposure time of the fluorescence-imaging unit is changed, it is possible to standardize the fluorescence image at a luminance value per unit time with the image-correction unit.

In the above-described aspect, the image-acquisition condition adjusting portion may adjust a gain factor of the fluorescence-imaging unit, and the image-correction unit may divide the luminance value of the fluorescence image by the gain factor.

Configuring in this way, it is possible to adjust the brightness of the fluorescence image by using the image-acquisition condition adjusting portion by changing the gain factor of the fluorescence-imaging unit. In addition, even if the gain factor of the fluorescence-imaging unit is changed, it is possible to standardize the fluorescence image at a certain luminance value per multiplication value with the image-correction unit.

In the above-described aspect, the image-acquisition condition adjusting portion may adjust excitation-light intensity from the illumination portion, and the image-correction unit may divide the luminance value of the fluorescence image by the excitation-light intensity.

Configuring in this way, it is possible to adjust the brightness of the fluorescence image by using the image-acquisition condition adjusting portion by changing the intensity of the excitation light radiated on the subject. In addition, even if the excitation-light intensity from the illumination portion is changed, it is possible to standardize the fluorescence image at a certain luminance value per excitation-light intensity with the image-correction unit.

In the above-described aspect, an image-acquisition condition adjusting portion that adjusts the image acquisition condition on the basis of the luminance value of the reference image acquired by the return-light imaging unit is provided, wherein the image-correction unit may normalize the luminance of the reference image by the image acquisition condition.

Configuring in this way, it is possible to obtain a reference image having suitable brightness by using the image-acquisition condition adjusting portion regardless of the luminance of the return light returning from the subject. In this case, by normalizing the luminance of the reference image by the image acquisition condition with the image-correction unit, even when the image acquisition condition of the image-acquisition condition adjusting portion is changed, it is possible to standardize the luminance value of the reference image.

In the above-described aspect, the image-acquisition condition adjusting portion may adjust exposure time of the return-light imaging unit, and the image-correction unit divides the luminance value of the reference image by the exposure time.

Configuring in this way, it is possible to adjust the brightness of the reference image by changing the exposure time of the return-light imaging unit with the image-acquisition condition adjusting portion. In addition, even if the exposure time of the return-light imaging unit is changed, it is possible to standardize the reference image at a luminance value per unit time with the image-correction unit.

In the above-described aspect, the image-acquisition condition adjusting portion may adjust a gain factor of the return-light imaging unit, and the image-correction unit may divide the luminance value of the reference image by the gain factor.

Configuring in this way, it is possible to adjust the brightness of the reference image by changing the gain factor of the return-light imaging unit with the image-acquisition condition adjusting portion. In addition, even if the gain factor of the return-light imaging unit is changed, it is possible to standardize the reference image at a certain luminance value per multiplication value with the image-correction unit.

In the above-described aspect, the image-acquisition condition adjusting portion adjusts illumination light intensity from the illumination portion, and the image-correction unit divides the luminance value of the reference image by the illumination light intensity.

Configuring in this way, it is possible to adjust the brightness of the reference image by using the image-acquisition condition adjusting portion by changing the intensity of the return light returning from the subject. In addition, even if the illumination light intensity from the illumination portion is changed, it is possible to standardize the reference image at a certain luminance value per unit of illumination light intensity with the image-correction unit.

A sixth aspect of the present invention is a fluoroscopy system comprising a fluoroscopy apparatus according to the above-mentioned present invention and a calibration device that calibrates the fluoroscopy apparatus, wherein the calibration device is provided with a standard specimen and an observation-state setting mechanism that changeably sets an observation distance of the fluoroscopy apparatus relative to the standard specimen, and wherein the fluoroscopy apparatus or the calibration device is provided with an exponent calculating unit that calculates the first exponent and the second exponent on the basis of the observation distance set by the observation-state setting mechanism and the fluorescence image and the reference image acquired by imaging the standard specimen with the fluoroscopy apparatus.

According to this aspect, by calibrating the fluoroscopy apparatus with the calibration device prior to the fluorescence observation, it is possible to calculate the first exponent and the second exponent in the fluoroscopy apparatus more precisely by the operation of the exponent calculating unit on the basis of the image acquired using the standard specimen.

A seventh aspect of the present invention is a fluoroscopy system comprising a fluoroscopy apparatus according to the above-mentioned present invention and a calibration device that calibrates the fluoroscopy apparatus, wherein the calibration device is provided with a standard specimen and an observation-state setting mechanism that changeably sets an observation distance of the fluoroscopy apparatus relative to the standard specimen, and wherein the fluoroscopy apparatus or the calibration device is provided with a correction-factor calculating unit that calculates the first correction factor and the second correction factor on the basis of the observation distance set by the observation-state setting mechanism and the fluorescence image and the reference image acquired by imaging the standard specimen with the fluoroscopy apparatus.

According to this aspect, by calibrating the fluoroscopy apparatus with the calibration device prior to the fluorescence observation, it is possible to calculate the first correction factor and the second correction factor in the fluoroscopy apparatus more precisely by the operation of the exponent calculating unit on the basis of the image acquired using the standard specimen.

An eighth aspect of the present invention is a fluorescence-image processing method for performing the following correction processing on a fluorescence image acquired by imaging fluorescence produced at a subject by radiating excitation light from an illumination portion onto the subject by using a reference image acquired by imaging return light returning from the subject when the subject is irradiated with illumination light from the illumination portion:

$$FL_{revised} = FL_{after}/RL_{after},$$

where, $FL_{revised}$ is a luminance value of a fluorescence image after correction, $FL_{after} = A \times FL_{before}^{x}$, $RL_{after} = B \times RL_{before}^{y}$, $FL_{before}$ and $RL_{before}$ before are luminance values of the acquired fluorescence image and reference image, A and B are constants, x is a reciprocal of an exponent obtained by a power approximation of a characteristic of luminance versus distance from the illumination portion to the subject, for the fluorescence image obtained by radiating excitation light of a prescribed intensity onto the subject, and y is a reciprocal of an exponent obtained by a power approximation of a characteristic of luminance versus distance from the illumination portion to the subject, for the reference image obtained by radiating illumination light of a prescribed intensity onto the subject.

A ninth aspect of the present invention is a fluorescence-image processing method for performing the following correction processing on a fluorescence image acquired by imaging fluorescence produced at a subject by radiating excitation light from an illumination portion onto the subject by using a reference image acquired by imaging return light returning from the subject when the subject is irradiated with illumination light from the illumination portion:

$$FL_{revised} = (FL_{after}/RL_{after})^{1/x},$$

where, $FL_{revised}$ is a luminance value of a fluorescence image after correction, $FL_{after} = A \times FL_{before}^{x}$, $RL_{after} = B \times RL_{before}^{y}$, $FL_{before}$ and $RL_{before}$ are luminance values of the acquired fluorescence image and reference image, A and B are constants, x is a reciprocal of an exponent obtained by a power approximation of a characteristic of luminance versus distance from the illumination portion to the subject, for the fluorescence image obtained by radiating excitation light of a prescribed intensity onto the subject, and y is a reciprocal of an exponent obtained by a power approximation of a characteristic of luminance versus distance from the illumination portion to the subject, for the reference image obtained by radiating illumination light of a prescribed intensity onto the subject.

A tenth aspect of the present invention is a fluorescence-image processing method for performing the following correction processing on a fluorescence image acquired by imaging fluorescence produced at a subject by radiating excitation light from an illumination portion onto the subject by using a reference image acquired by imaging return light returning from the subject when the subject is irradiated with illumination light from the illumination portion:

$$FL_{revised} = FL_{before}/RL_{after},$$

where, $FL_{revised}$ is a luminance value of a fluorescence image after correction, $RL_{after} = B \times RL_{before}^{y}$, $FL_{before}$ and $RL_{before}$ before are luminance values of the acquired fluorescence image and reference image, B is a constant;

y is a value obtained by dividing a first exponent obtained by a power approximation of a characteristic of luminance versus distance from the illumination portion to the subject, for the fluorescence image obtained by radiating excitation light of a prescribed intensity onto the subject, by a second exponent obtained by a power approximation of a characteristic of luminance versus distance from the illumination portion to the subject, for the reference image obtained by radiating illumination light of a prescribed intensity onto the subject.

An eleventh aspect of the present invention is a fluorescence-image processing method for performing the following correction processing on a fluorescence image acquired by imaging fluorescence produced at a subject by radiating excitation light from an illumination portion onto the subject by using a reference image acquired by imaging return light returning from the subject when the subject is irradiated with illumination light from the illumination portion:

$$FL_{revised} = FL_{after}/RL_{before},$$

where, $FL_{revised}$ is a luminance value of a fluorescence image after correction, $FL_{after} = B \times FL_{before}^{1/y}$, $FL_{before}$ and $RL_{before}$ before are luminance values of the acquired fluorescence image and reference image, B is a constant, y is a value obtained by dividing a first exponent obtained by a power approximation of a characteristic of luminance versus distance from the illumination portion to the subject, for the fluorescence image obtained by radiating excitation light of a prescribed intensity onto the subject, by a second exponent obtained by a power approximation of a characteristic of luminance versus distance from the illumination portion to the subject, for the reference image obtained by radiating illumination light of a prescribed intensity onto the subject.

BRIEF DESCRIPTION OF DRAWINGS

FIG. 7 is a diagram showing an example of a concentration conversion table provided in an image-combining unit of the fluoroscopy apparatus in FIG. 1.

FIG. 16 is a diagram showing a state in which simultaneous observation of two identical standard specimens positioned at different observation distances is performed with a fluoroscopy apparatus according to a fifth modification of the first embodiment of the present invention.

FIG. 21 is a diagram showing a standard deviation of $FL/RL^a$ in a region of interest at every correction factor.

DESCRIPTION OF EMBODIMENTS

First Embodiment

A fluoroscopy system, a fluoroscopy apparatus, and a fluorescence-image processing method according to a first embodiment of the present invention will be described below with reference to the drawings.

Figure 1:
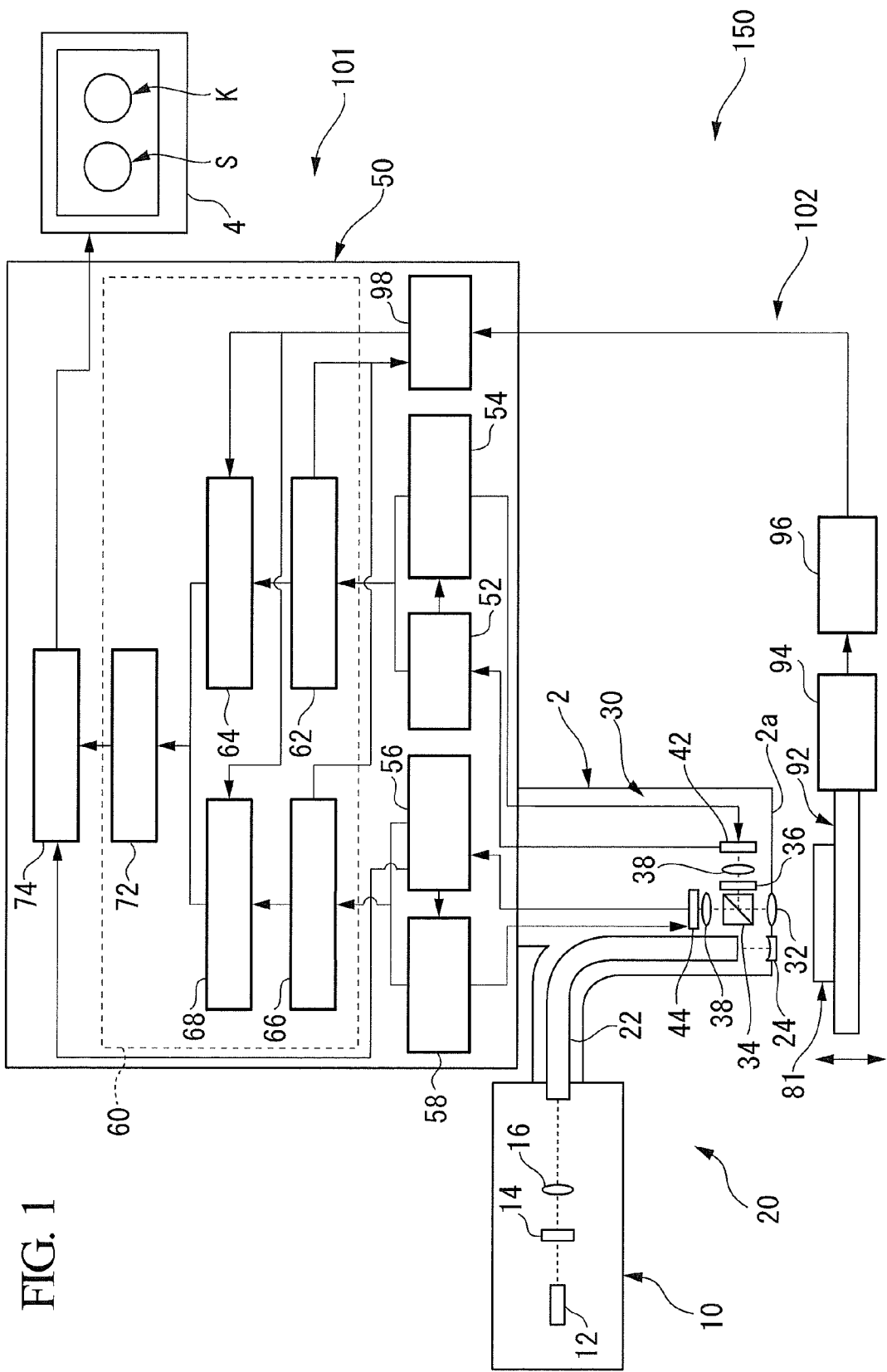
FIG. 1 is a block diagram showing, in outline, the configuration of a fluoroscopy apparatus according to a first embodiment of the present invention.

As shown in FIG. 1, a fluoroscopy system 150 according to this embodiment is provided with a fluoroscopy apparatus 101 and a calibration device 102 that is combined with the fluoroscopy apparatus 101. The fluoroscopy apparatus 101 is an endoscope apparatus and is provided with an elongated insertion portion 2 that is inserted inside a body cavity, an illumination unit (illumination portion) 20 that includes a light source 10 that emits illumination light from an end 2a of the insertion portion 2, an image-acquisition unit 30 that is disposed in the insertion portion 2 and acquires image information of an observation target site X, which is the subject, an image processing unit 50 that performs arithmetic processing of the image information acquired by the image-acquisition unit 30, and a monitor 4 that displays the images etc. that are processed by the image processing unit 50.

The light source 10 is provided with a xenon lamp 12 that emits illumination light, a filter 14 that extracts the white light (illumination light) containing the excitation light from the illumination light emitted from the xenon lamp 12, and a coupling lens 16 that focuses the white light containing the excitation light extracted by the filter 14. The filter 14 extracts, for example, the white light containing the excitation light in a wavelength band between 400 and 750 nm.

The illumination unit 20 is provided with a light guide fiber 22 that is disposed along a longitudinal direction of the insertion portion 2 over nearly the entire length thereof and that guides the white light containing the excitation light focused by a coupling lens 16 to the end 2a of the insertion portion 2, and a spreading lens 24 that is disposed on the end 2a of the insertion portion 2 and that spreads the white light containing the excitation light guided by the light guide fiber 22 to irradiate the observation target site X.

The image-acquisition unit 30 is provided with an objective lens 32 that collects return light returning from the observation target site X irradiated with the white light containing the excitation light by the illumination unit 20 and a dichroic mirror 34 that reflects light of the excitation wavelength or higher (the excitation light and fluorescence) in the return light collected by the objective lens 32, and that transmits white light having a wavelength shorter than the excitation wavelength. The objective lens 32 and the spreading lens 24 are arranged side-by-side on the end 2a of the insertion portion 2.

This image-acquisition unit 30 is provided with an excitation-light cut filter 36 that blocks the excitation light in the excitation light and fluorescence reflected by the dichroic mirror 34 and that transmits only the fluorescence (for example, near-infrared fluorescence), two focusing lenses 38 that respectively focus the fluorescence transmitted through this excitation-light cut filter 36 and the white light transmitted through the dichroic mirror 34, a fluorescence-imaging unit 42 that images the fluorescence focused by the focusing lenses 38 to obtain the fluorescence image information, and a white-light-imaging unit (return-light imaging unit) 44 that images the white light focused by the focusing lenses 38 to obtain the reference image information.

The excitation-light cut filter 36 only transmits, for example, fluorescence in the wavelength band between 765 and 850 nm.

The fluorescence-imaging unit 42 is, for example, a high-sensitivity monochrome CCD for fluorescence. The white-light-imaging unit 44 is, for example, a color CCD for white light and is provided with a mosaic filter (not shown).

The image processing unit 50 is provided with a fluorescence exposure-time adjusting portion (image-acquisition condition adjusting portion) 54 that adjusts the exposure time (image acquisition condition) of the fluorescence-imaging unit 42 and a fluorescence-image generating unit 52 that generates a two-dimensional fluorescence image on the basis of the fluorescence image information acquired by the fluorescence-imaging unit 42, a white-light exposure-time adjusting unit (image-acquisition condition adjusting portion) 58 that adjusts the exposure time (image acquisition condition) of the white-light-imaging unit 44 and a reference-image generating unit 56 that generates a two-dimensional reference image on the basis of the reference image information acquired by the white-light-imaging unit 44, and an image-correction unit 60 that corrects the fluorescence image generated by the fluorescence-image generating unit 52 using the reference image generated by the reference-image generating unit 56.

The fluorescence exposure-time adjusting portion 54 adjusts the exposure time of the fluorescence-imaging unit 42 on the basis of the luminance values of the fluorescence image generated by the fluorescence-image generating unit 52.

Similarly, the white-light exposure-time adjusting unit 58 adjusts the exposure time of the white-light-imaging unit 44 on the basis of the luminance values of the reference image generated by the reference-image generating unit 56.

The image-correction unit 60 is provided with a fluorescence-image normalization portion 62 that normalizes the luminance of the fluorescence image generated by the fluorescence-image generating unit 52 and a fluorescence-image preprocessing section 64 that performs arithmetic processing on the fluorescence image whose luminance is normalized; a reference-image normalization portion 66 that normalizes the luminance of the reference image obtained by the reference-image generating unit 56 and a reference-image preprocessing section 68 that performs arithmetic processing on the reference image whose luminance is normalized; and a division processing unit 72 that obtains a corrected fluorescence image K by dividing the correction fluorescence image obtained by the fluorescence-image preprocessing section 64 by the correction reference image obtained by the reference-image preprocessing section 68.

The fluorescence-image normalization portion 62 reads out the luminance value of the fluorescence image from the fluorescence-image generating unit 52 and divides it by the exposure time of the fluorescence-imaging unit 42 set by the fluorescence exposure-time adjusting portion 54.

The fluorescence-image preprocessing section 64 obtains the correction fluorescence image by raising the normalized luminance value of the fluorescence image to the power of the reciprocal $1/\alpha$ (or $-1/\alpha$) of a first exponent $\alpha$ that is obtained by a power approximation of a distance characteristic of luminance versus observation distance Dn for the fluorescence image, which is obtained by the fluorescence-imaging unit 42 by radiating the excitation light of a prescribed intensity onto the observation target site X and which is normalized by the fluorescence-image normalization portion 62. Specifically, the power computation shown below is performed:

$$FL_{after} = A \times FL_{before}^{x} \tag{1}$$

Here, $FL_{after}$ is a luminance value of the correction fluorescence image, $FL_{before}$ is a luminance value of the fluorescence image, x is $1/\alpha$ or $-1/\alpha$, $\alpha$ is a first exponent, and A is a constant.

By performing this power computation, the correction fluorescence image whose luminance is proportional to (with $-1/\alpha$, inversely proportional to) the variation of the distance is obtained.

Similarly, the reference-image normalization portion 66 reads out the luminance information of the reference image from the reference-image generating unit 56 and divides it by the exposure time of the white-light-imaging unit 44 set by the white-light exposure-time adjusting unit 58.

In addition, the reference-image preprocessing section 68 obtains the correction reference image by raising the normalized luminance value of the reference image to the power of reciprocal $1/\beta$ (or $-1/\beta$) of a second exponent $\beta$ that is obtained by a power approximation of a distance characteristic of luminance versus observation distance Dn for the reference image, which is obtained by the white-light-imaging unit 44 by radiating the white light of a prescribed intensity onto the observation target site X and which is normalized by the reference-image normalization portion 66. Specifically, the power computation shown below is performed:

$$RL_{after} = B \times RL_{before}^{y} \tag{2}$$

Here $RL_{after}$ is a luminance value of the correction reference image, $RL_{before}$ is a luminance value of the reference image, y is $1/\beta$ or $-1/\beta$, $\beta$ is a second exponent, and B is a constant.

By performing this power computation, the correction reference image whose luminance is proportional to (with $-1/\beta$, inversely proportional to) the variation of the distance is obtained.

Figure 2:
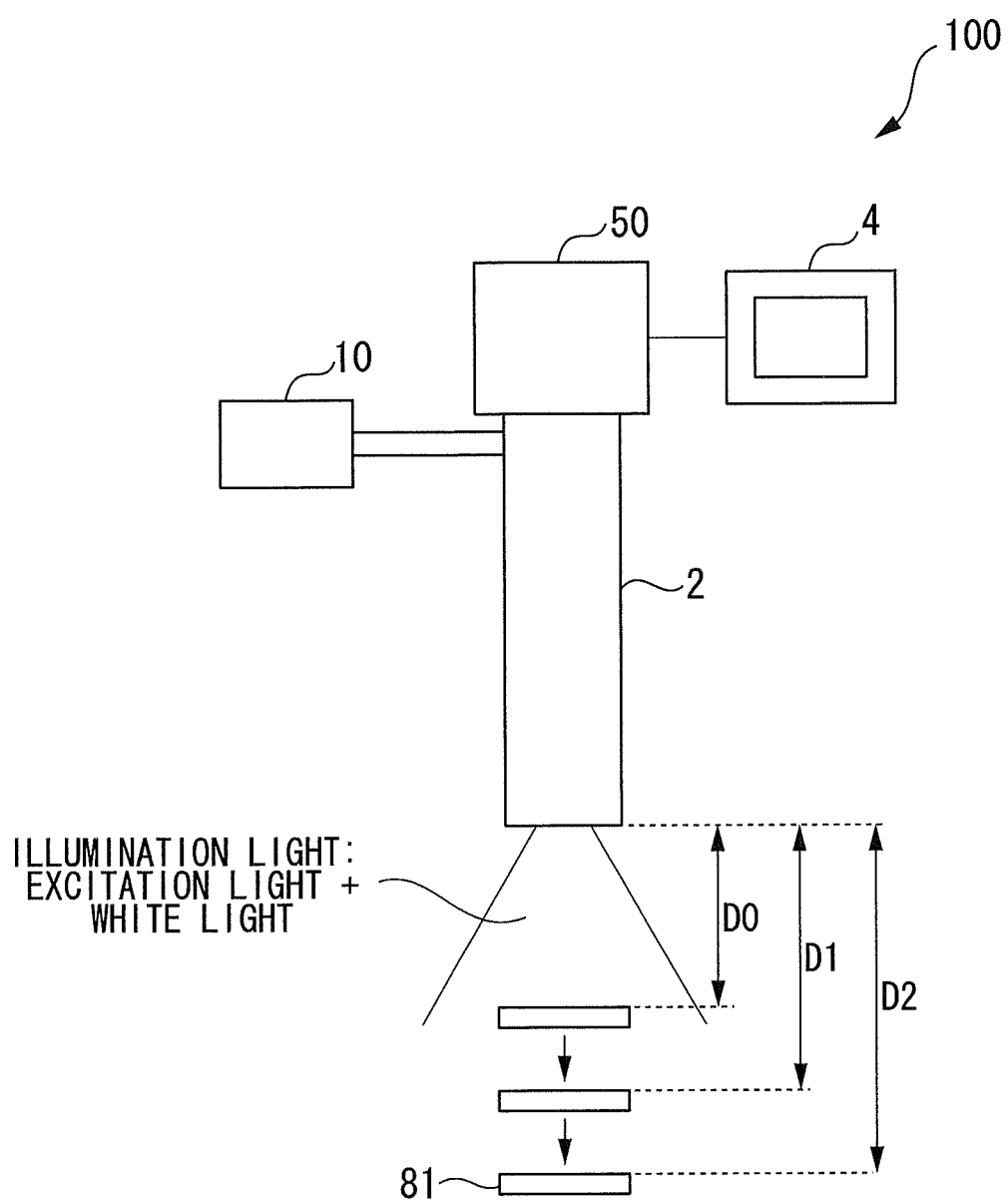
FIG. 2 is a diagram showing a state in which the observation distance between an insertion portion of the fluoroscopy apparatus in FIG. 1 and a standard specimen is changed.

In this case, based on a determination made prior to the fluorescence observation, the first exponent $\alpha$ and the second exponent $\beta$ are decided, as described below, by, as shown in FIG. 2, disposing a standard specimen 81 so as to oppose the end 2a of the insertion portion 2, and using the calibration device 102.

The calibration device 102 is provided with a translation stage (observation-state setting mechanism) 92 that changes the distance Dn (hereinafter referred to as "observation distance") between the end 2a of the insertion portion 2 and the standard specimen 81, a stage controller 94 that controls the position of the translation stage 92, a distance-information detector 96 that detects the distance information of the observation distance Dn, and a dependency-constant determining unit (exponent calculating unit) 98 that calculates the first exponent $\alpha$ and the second exponent $\beta$.

The dependency-constant determining unit 98 calculates the first exponent $\alpha$ and the second exponent $\beta$ on the basis of the normalized fluorescence image and reference image sent from the fluorescence-image normalization portion 62 and the reference-image normalization portion 66, respectively, and on the basis of the distance information detected by the distance-information detector 96.

As the standard specimen 81, for example, one having an optical characteristic close to that of a living body, such as tissue from a pig large intestine, injected with fluorescent dye is desirable.

Figure 3:
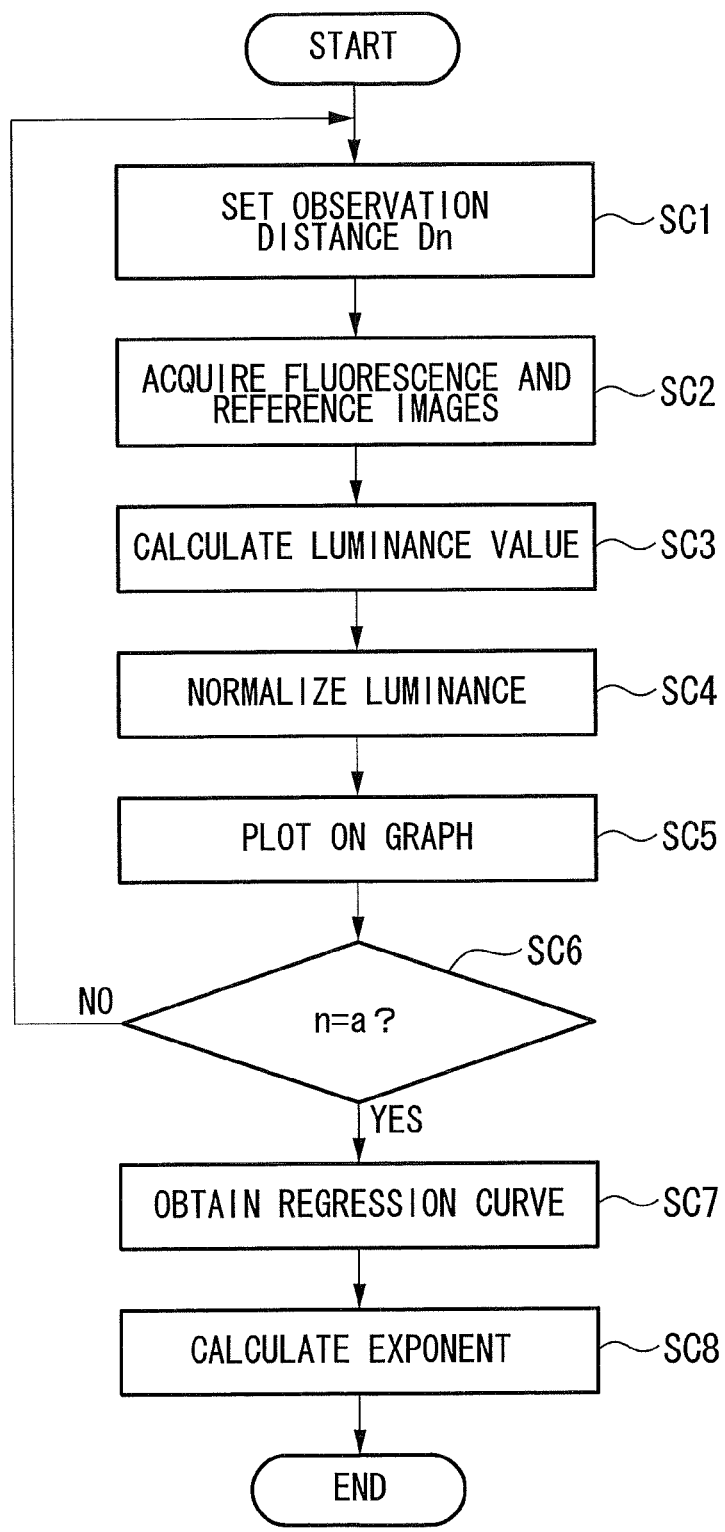
FIG. 3 is a flowchart showing a method of calculating an exponent in the fluoroscopy apparatus in FIG. 1.

The method of calculating the first exponent $\alpha$ and the second exponent $\beta$ in the dependency-constant determining unit 98 will be described below with reference to a flowchart in FIG. 3.

The observation distance Dn is first set by operating the stage controller 94 (step SC1), and the observation distance Dn at this time is detected by the distance-information detector 96 and sent to the dependency-constant determining unit 98. In this state, the white light containing the excitation light is radiated onto the standard specimen 81 from the illumination unit 20. Then, the fluorescence and the white light are captured respectively with the fluorescence-imaging unit 42 and the white-light-imaging unit 44, and the fluorescence image and the reference image are obtained by the fluorescence-image generating unit 52 and the reference-image generating unit 56 (step SC2).

Next, the average values of the luminance values of regions that are determined in advance (hereinafter referred to as "regions of interest") of the acquired fluorescence image and reference image are calculated (step SC3).

The method of obtaining the luminance values is explained with the following reference example as an illustration.

For example, as shown in FIG. 2, the illumination light is radiated onto the standard specimen 81 while changing the observation distance Dn to D0, D1, and D2 (D0<D1<D2) to obtain the fluorescence images such as those shown in FIGS. 4A to 4C and FIGS. 5A to 5C. In FIG. 2, reference sign 83 is a field of view of the fluorescence-imaging unit 42 and reference sign 85 is a region of interest.

Figure 4A:
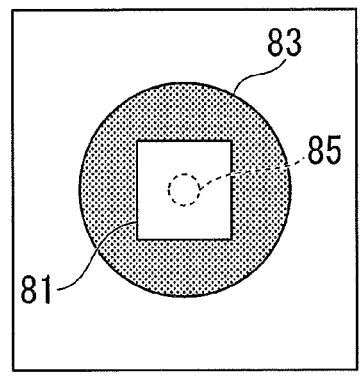
FIG. 4A is a diagram showing an image with observation distance D0, in the case where the size of a region of interest is not changed.
Figure 4B:
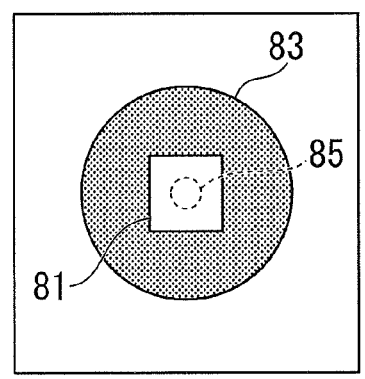
FIG. 4B is a diagram showing an image with observation distance D1, in the case where the size of a region of interest is not changed.
Figure 4C:
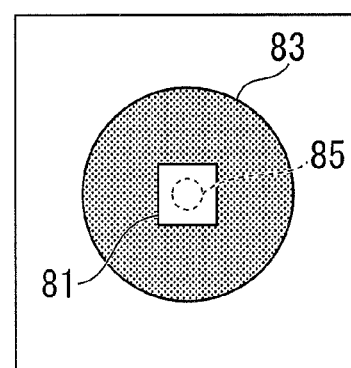
FIG. 4C is a diagram showing an image with observation distance D2, in the case where the size of a region of interest is not changed.
Figure 5A:
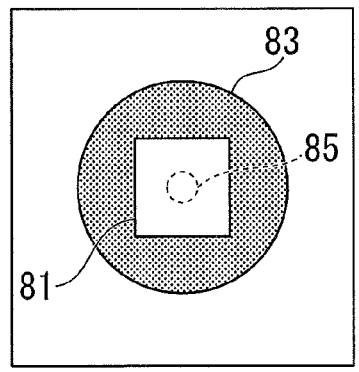
FIG. 5A is a diagram showing an image with observation distance D0, in the case where the size of a region of interest is changed.
Figure 5B:
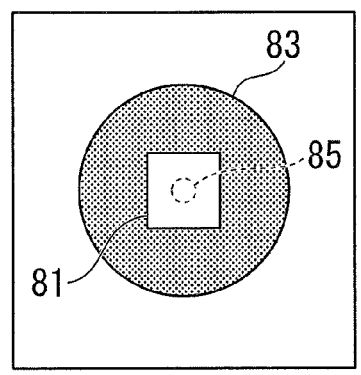
FIG. 5B is a diagram showing an image with observation distance D1, in the case where the size of a region of interest is changed.
Figure 5C:
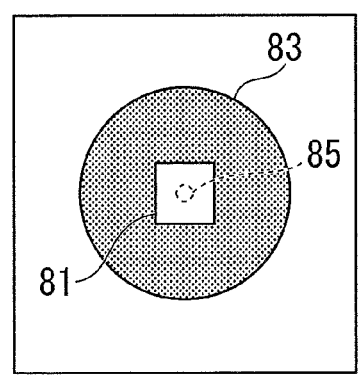
FIG. 5C is a diagram showing an image with observation distance D2, in the case where the size of a region of interest is changed.

If the fluorescence intensity in the standard specimen 81 is constant, in other words, for example, if the surface of the standard specimen 81, which is the subject, is substantially flat, as shown in FIGS. 4A to 4C, the luminance value is calculated by making the size of the region of interest 85 constant regardless of the observation distance Dn. On the other hand, if the fluorescence intensity in the standard specimen 81 is not constant, in other word, for example, if there are irregularities on the surface of the standard specimen 81 and if there are nonuniformities in the fluorescence distribution in the standard specimen 81, as shown in FIGS. 5A to 5C, the luminance value is calculated by changing the size of the region of interest 85 in accordance with the observation distance Dn. By changing the size of the region of interest 85, it is possible to obtain the luminance value of the same site even when the observation distance Dn is changed.

Next, the average values of the luminance values in the regions of interest, which are calculated from the fluorescence image and reference image, are divided by the exposure time and normalized by the fluorescence-image normalization portion 62 and the reference-image normalization portion 66 (step SC4), respectively, and thereafter, they are sent to the dependency-constant determining unit 98, and the luminance values are plotted in association with the distance information (step SC5).

Figure 17A:
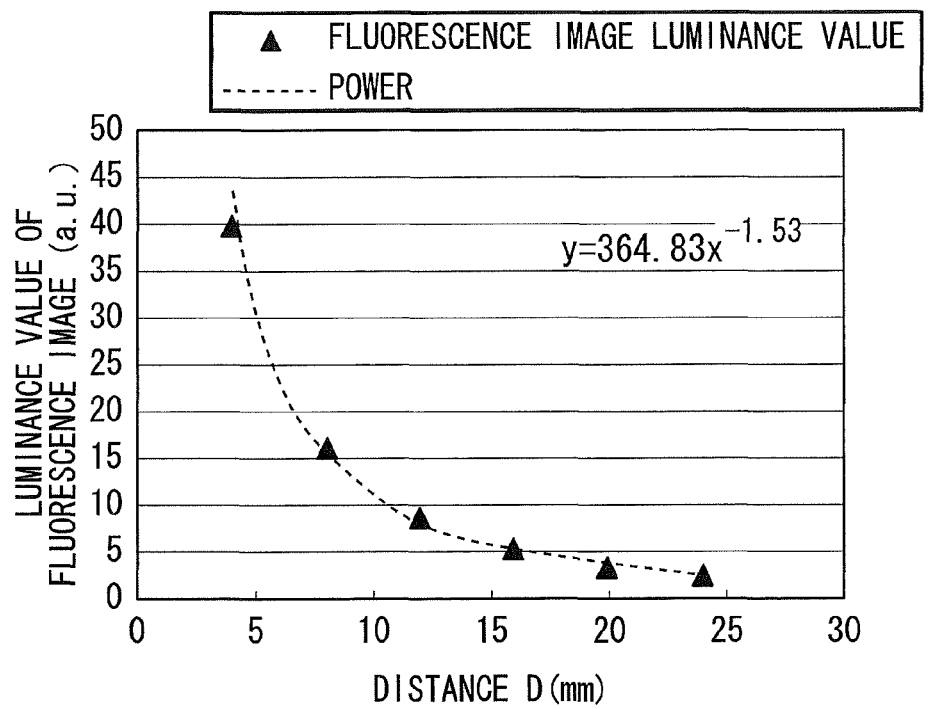
FIG. 17A is a diagram showing the relationship between the luminance value of a fluorescence image obtained by the fluoroscopy apparatus according to the fifth modification of the first embodiment of the present invention and the observation distance.
Figure 17B:
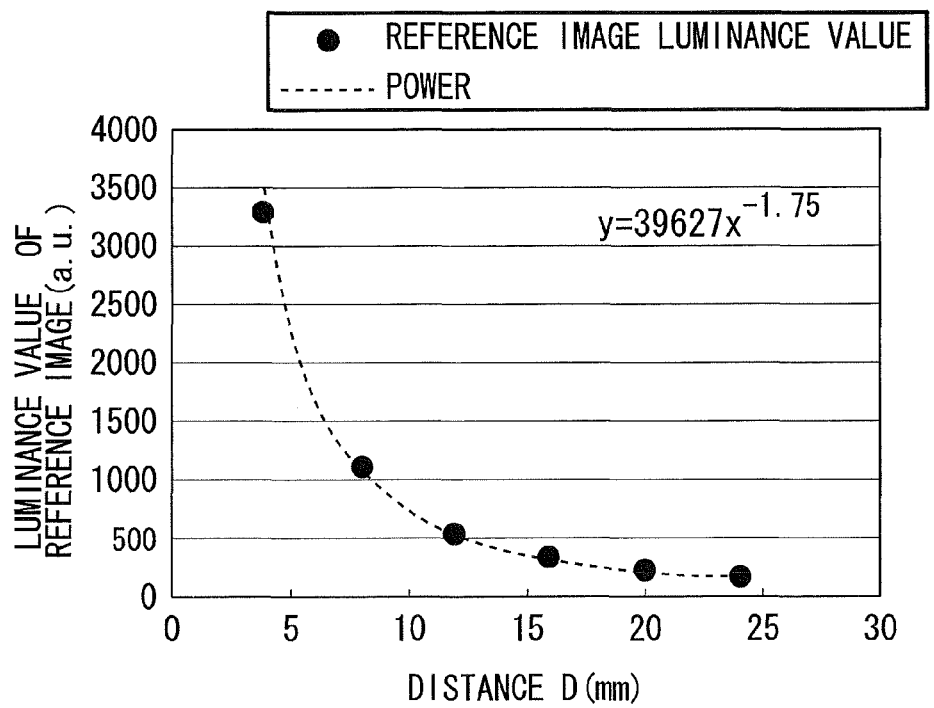
FIG. 17B is a diagram showing the relationship between the luminance value of a reference image obtained by the fluoroscopy apparatus according to the fifth modification of the first embodiment of the present invention and the observation distance.

The stage controller 94 repeats the above-described steps SC1 to SC6 multiple times for a predetermined number of times a (a is at least two or more) (step SC6). For example, the observation distance Dn is changed to D0 and D1, for example, a regression curve is obtained by a power approximation of the obtained distance characteristics, in other words, by performing regression to power functions $D^\alpha$ and $D^\beta$ (step SC7), and thereby, the first exponent $\alpha$ and the second exponent $\beta$ that indicate the dependencies on the observation distance Dn are calculated (step SC8). The results of the determination of the first exponent $\alpha$ and the second exponent $\beta$ from the regression curve, as the reference examples, are shown in FIGS. 17A and 17B. In FIGS. 17A and 17B, the vertical axis indicates the luminance value in the fluorescence image or the reference image and the horizontal axis indicates the observation distance Dn.

By doing so, it is possible to determine the observation distance Dn and corresponding accurate exponents for the fluorescence image and the reference image with the dependency-constant determining unit 98. The first exponent $\alpha$ and the second exponent $\beta$ determined by the dependency-constant determining unit 98 are sent to the fluorescence-image preprocessing section 64 and the reference-image preprocessing section 66, respectively.

In this embodiment, the distance-information detector 96 may be omitted, and distance information of the observation distance Dn may be input to the dependency-constant determining unit 98 manually.

Figure 6:
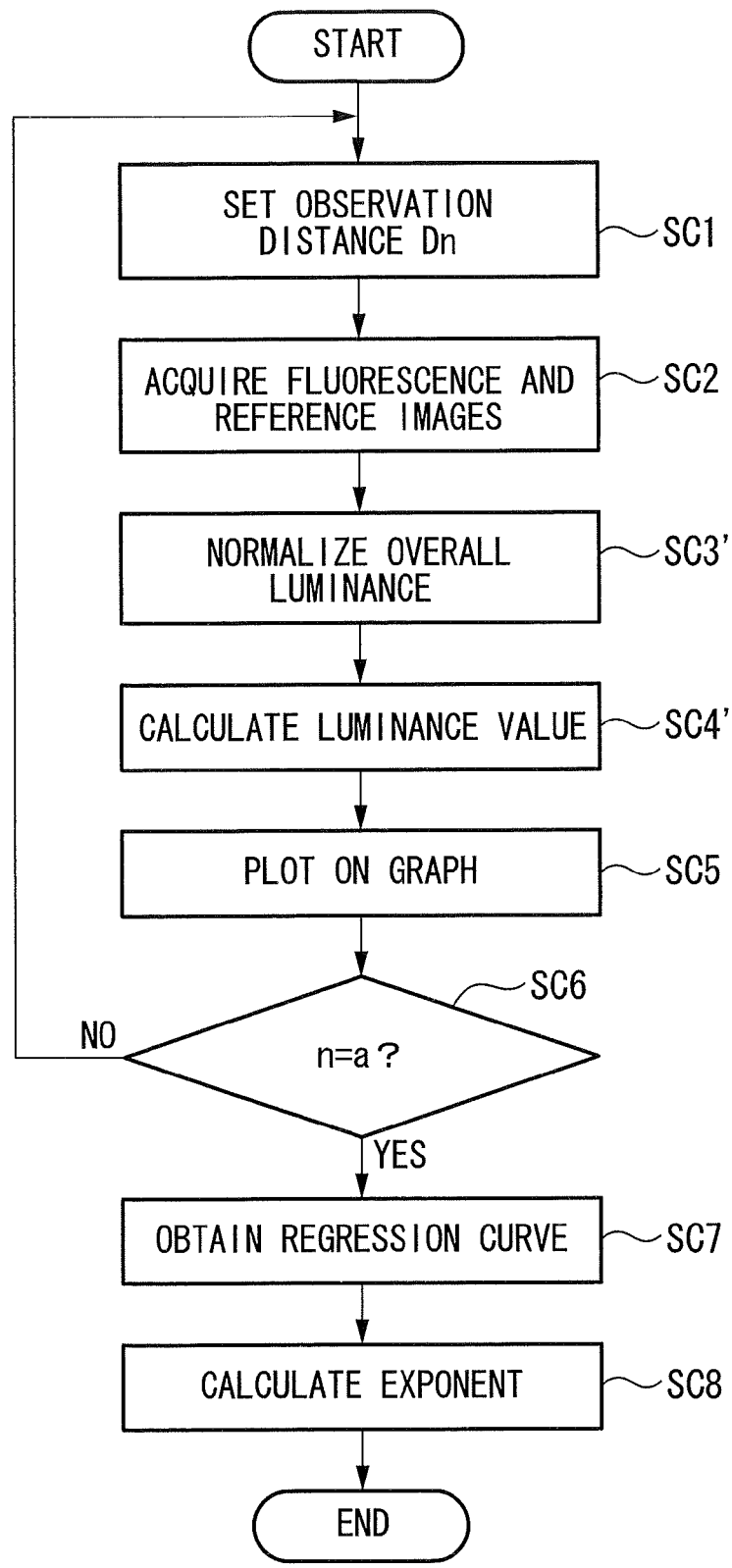
FIG. 6 is a flowchart showing another method of calculating an exponent in the fluoroscopy apparatus according to the first embodiment of the present invention.

In addition, in this embodiment, although the average values of the luminance values of the regions of interest in the fluorescence image and the reference image are calculated before the normalization (see step SC3 in FIG. 3), and thereafter, the average values are normalized by treating them as the luminance values and dividing them by the exposure time (see SC4 in FIG. 3), instead of this, as shown in the flowchart in FIG. 6, for example, the normalization may be performed by dividing the luminance of the whole fluorescence image and the luminance of the whole reference image by the exposure time, respectively (step SC3'), and thereafter, the average values of the normalized luminance values of the regions of interest in the fluorescence image and the reference image may be calculated (step SC4').

In addition, the image processing unit 50 is provided with an image-combining unit 74 that generates an image by combining the reference image S generated by the reference-image generating unit 56 and the corrected fluorescence image K generated by an image-correction unit 75. The image-combining unit 74 combines the corrected fluorescence image K obtained by the division processing unit 72 and the reference image S generated by the reference-image generating unit 56 such that the combined images are arranged in parallel and simultaneously displayed on the monitor 4. In addition, as shown in FIG. 7, the image-combining unit 74 has a concentration conversion table 87 in which the luminance values of the corrected fluorescence image K and the amount of fluorescent agent present (in other words, the concentration of fluorescent agent) are associated with each other, which allows the fluorescence concentration in a specific region to be displayed on the monitor 4.

The operation of the thus-configured fluoroscopy apparatus 101 and fluorescence-image processing method according to this embodiment will be described.

In order to perform observation of, for example, an observation target site X in a body cavity of a living body using the fluoroscopy apparatus 101 according to this embodiment, the insertion portion 2 is inserted into the body cavity, and the end 2a is directed so as to oppose the observation target site X.

In this state, the illumination unit 20 is operated, and the white light containing the excitation light, which is emitted from the xenon lamp 12 and extracted by the filter 14, is focused by the coupling lens 16 so as to enter the light guide fiber 22. The white light containing the excitation light that has entered the light guide fiber 22 is guided to the end 2a of the insertion portion 2, is spread by the spreading lens 24, and is radiated onto the observation target site X.

In the observation target site X, the fluorescent agent contained therein is excited by the excitation light, emitting fluorescence, and the white light is reflected at the surface of the observation target site X. The fluorescence and the return light from the white light are collected by the objective lens 32 of the insertion portion 2 and are split into different wavelengths by the dichroic mirror 34.

At the dichroic mirror 34, the light of the excitation wavelength or higher, in other words, the excitation light, and fluorescence are reflected, and the white light having a shorter wavelength than the excitation wavelength is transmitted.

The excitation light among the excitation light and fluorescence reflected at the dichroic mirror 34 is removed by the excitation-light cut filter 36, and only the fluorescence is focused by the focusing lens 38. The fluorescence is captured by the fluorescence-imaging unit 42 and is obtained as the fluorescence image information.

In addition, the white light transmitted through the dichroic mirror 34 is focused by the focusing lens 38, is captured by the white-light-imaging unit 44, and is obtained as the reference image information.

Either fluorescence image information or the reference image information can be obtained before the other, or both can be obtained simultaneously.

Figure 8:
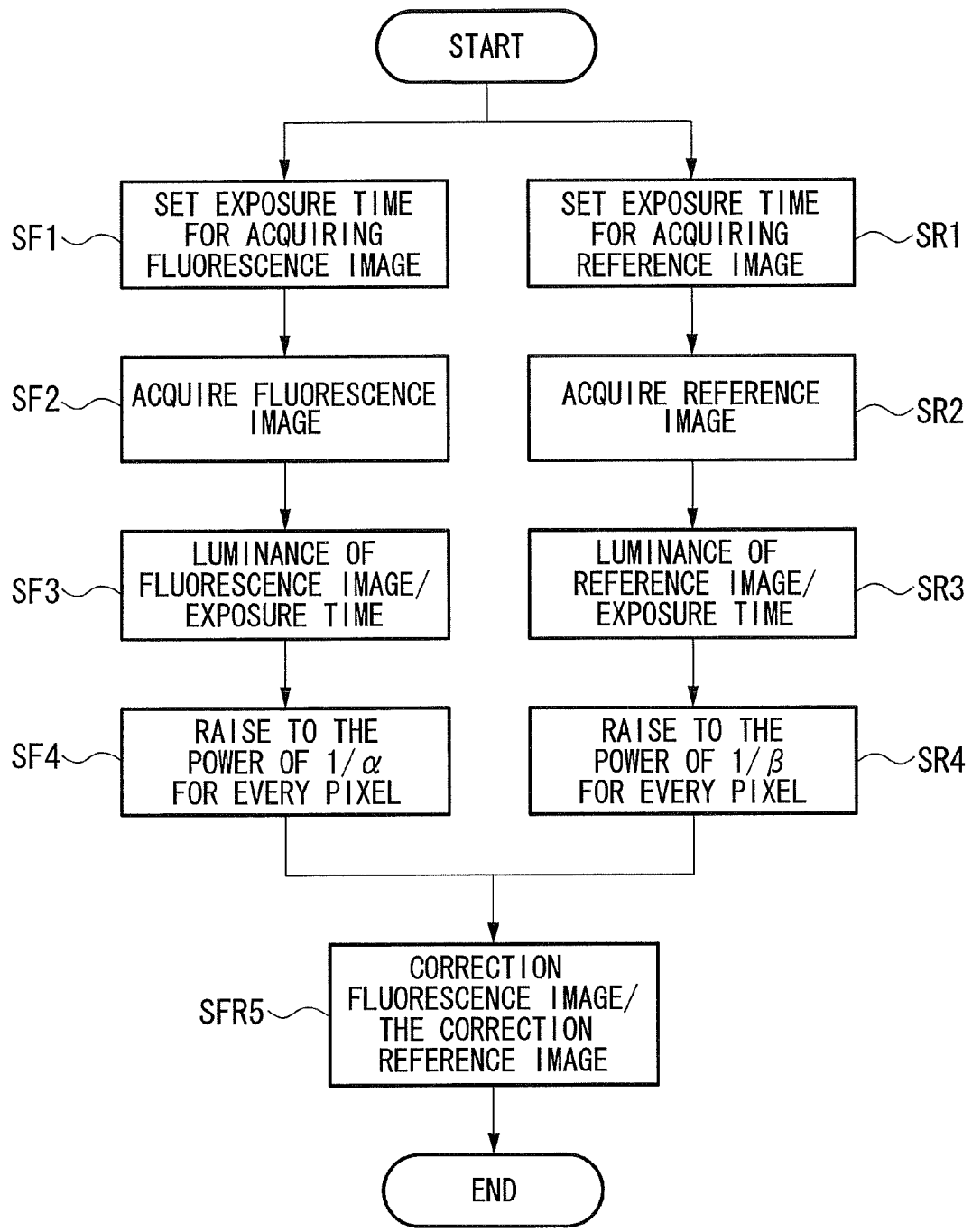
FIG. 8 is a flowchart of image processing in the image processing unit in FIG. 1.

The fluorescence image information obtained by the fluorescence-imaging unit 42 and the reference image information obtained by the white-light-imaging unit 44 are individually input to the image processing unit 50 and subjected to image processing. The image processing in the image processing unit 50 will be described below with reference to a flowchart in FIG. 8.

In the image processing unit 50, the fluorescence image information is input to the fluorescence-image generating unit 52, where a two-dimensional fluorescence image is generated. In this case, the exposure time of the fluorescence-imaging unit 42 is set by the fluorescence exposure-time adjusting portion 54 on the basis of the luminance value of the fluorescence image generated by the fluorescence-image generating unit 52 (step SF1). By doing so, a fluorescence image having suitable brightness is obtained by the fluorescence-image generating unit 52 regardless of the luminance of the fluorescence emitted from the observation target site X (step SF2).

Similarly, the reference image information is input to the reference-image generating unit 56, where a two-dimensional reference image is generated. In this case, the exposure time of the white-light-imaging unit 44 is adjusted by the white-light exposure-time adjusting unit 58 on the basis of the luminance value of the reference image generated by the reference-image generating unit 56 (step SR1). By doing so, a reference image having suitable brightness is obtained by the reference-image generating unit 56 regardless of the luminance of the white light returned from the observation target site X (step SR2).

The fluorescence image generated by the fluorescence-image generating unit 52 and the reference image generated by the reference-image generating unit 56 are individually sent to the image-correction unit 60.

In the image-correction unit 60, first, the fluorescence-image normalization portion 62 divides the luminance value of the fluorescence image by the exposure time of the fluorescence-imaging unit 42 (step SF3). By doing so, the differences in the exposure time in the fluorescence image are normalized, and the fluorescence image is standardized at luminance value per unit time. In addition, the reference-image normalization portion 66 divides the luminance value of the reference image by the exposure time of the white-light-imaging unit 44 (step SR3). By doing so, the differences in the exposure time in the reference image are normalized, and the reference image is standardized at luminance value per unit time.

The fluorescence image whose luminance has been normalized by the fluorescence-image normalization portion 62 is sent to the fluorescence-image preprocessing section 64, and the reference image whose luminance has been normalized by the reference-image normalization portion 66 is sent to the reference-image preprocessing section 68.

Next, in the fluorescence-image preprocessing section 64, in accordance with the above-mentioned correction arithmetic expression (1), the luminance value of each pixel in the fluorescence image is raised to the power of the reciprocal $1/\alpha$ of the first exponent $\alpha$ (step SF4). By doing so, information related to the power of the distance is cancelled, and a correction fluorescence image in which the luminance is proportional to the variation of the distance is obtained. In addition, in the reference-image preprocessing section 68, in accordance with the above-mentioned correction arithmetic expression (2), the luminance value of each pixel in the reference image is raised to the power of the reciprocal $1/\beta$ of the second exponent $\beta$ (step SR4). By doing so, information related to the power of the distance is cancelled, and a correction reference image in which the luminance is proportional to the variation of the distance is obtained.

Figure 9A:
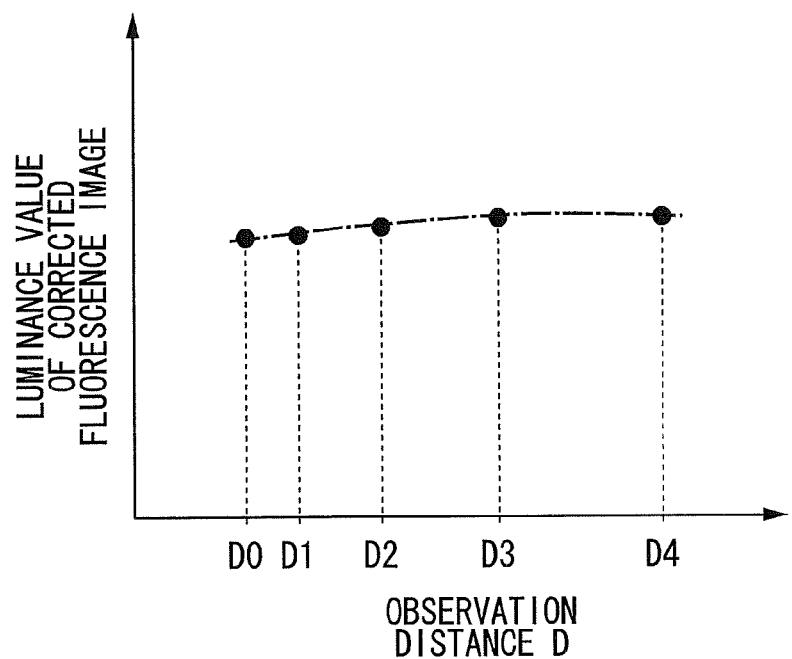
FIG. 9A is a graph showing the relationship between the luminance value of a corrected fluorescence image and the observation distance.

The correction fluorescence image and the correction reference image are individually sent to the division processing unit 72, where the correction fluorescence image is divided by the correction reference image (step SFR5). Since the correction fluorescence image and the correction reference image are related to each other such that the luminance is proportional to the variations of the distances by performing the above-mentioned power arithmetic processing, as shown in FIG. 9A, by dividing the correction fluorescence image by the correction reference image, it is possible to obtain a corrected fluorescence image K having quantitativeness, in which the dependencies on distance are cancelled, and the correction is achieved with a high accuracy.

The corrected fluorescence image K and the correction reference image obtained in the division processing unit 72 are sent to the image-combining unit 74. In the image-combining unit 74, the corrected fluorescence image K and the reference image S are combined and displayed on the monitor 4 simultaneously, and on the basis of the concentration conversion table 87, the fluorescence concentration in a specific region is displayed on the monitor 4.

As described above, according to the fluoroscopy apparatus 101 and fluorescence-image processing method of this embodiment, by subjecting the fluorescence image to the correction processing after processing the information related to the power of the distance contained in the fluorescence image and the reference image, it is possible to perform observation by obtaining the corrected fluorescence image K having high quantitativeness, in which the dependencies on distance of the fluorescence image and the reference image are cancelled. By doing so, it is possible to diagnose a lesion accurately from the luminance values of the corrected fluorescence image K.

Figure 9B:
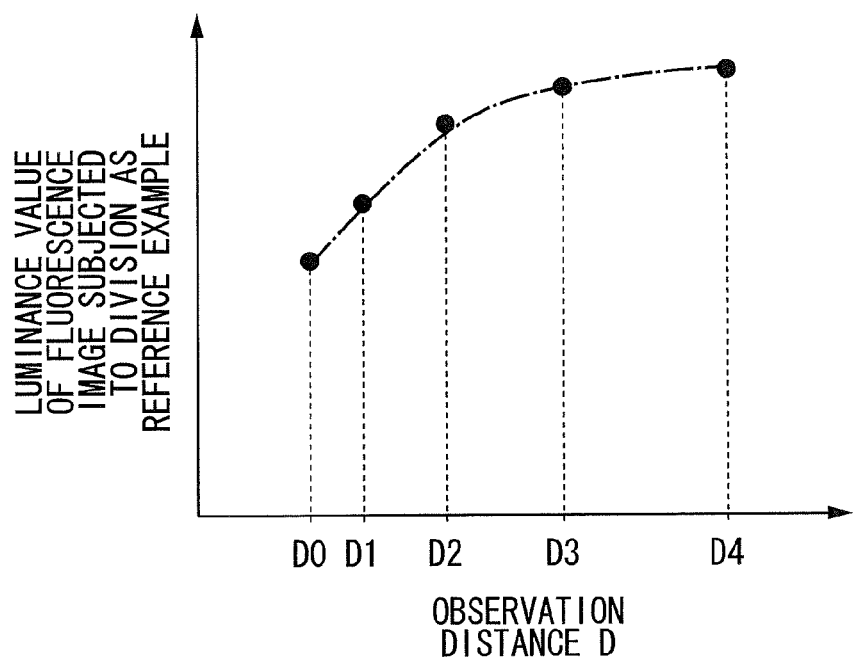
FIG. 9B is a graph showing, as a reference example, the relationship between the luminance value of a corrected fluorescence image and the observation distance.
Figure 10:
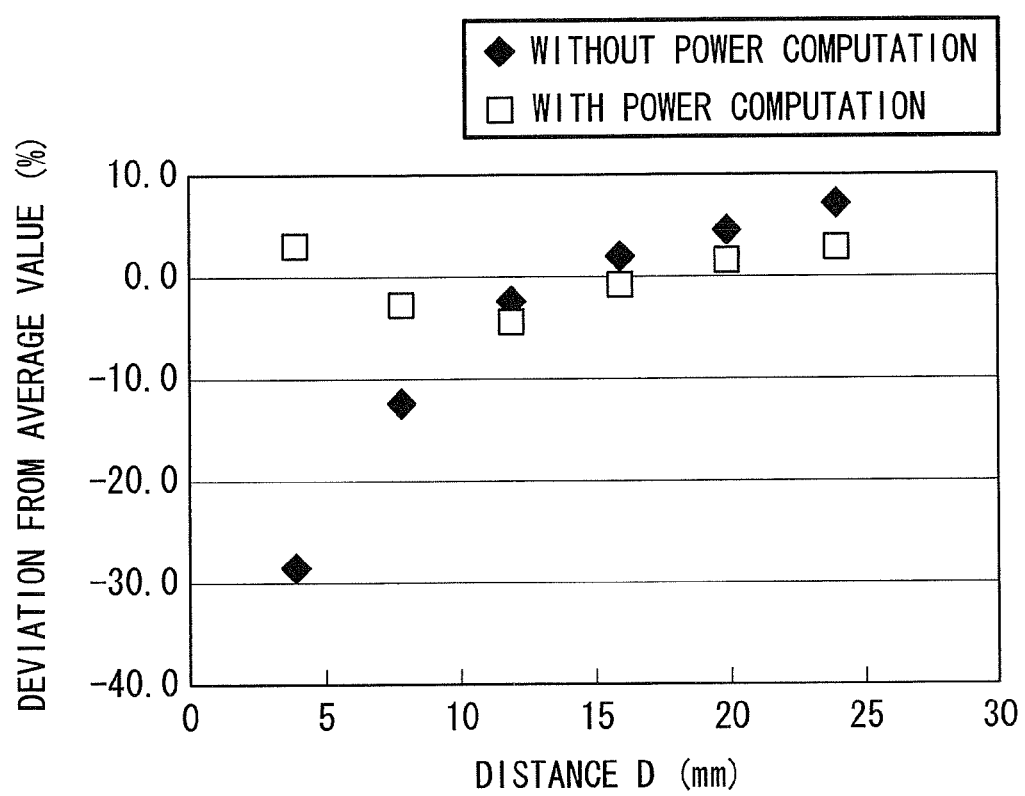
FIG. 10 is a graph comparing the deviation of luminance values of a fluorescence image subjected to power arithmetic processing and the deviation of luminance values of a fluorescence image without power arithmetic processing.

As a reference example, the relationship between the luminance value of the fluorescence image and the observation distance Dn when the fluorescence image is divided by the reference image without performing power arithmetic processing is shown in FIG. 9B. Since each of the fluorescence image and the reference image that is not subjected to power arithmetic processing contains the information related to the power of the distance, the dependencies on the distance cannot be completely cancelled by a simple division of the fluorescence image by the reference image, and the influence of distance remains in the divided fluorescence image. FIG. 10 shows the relationship between the observation distance Dn and the deviations from the average values of the luminance values of the fluorescence image with/without the power computation. In FIG. 10, the vertical axis indicates the deviation (%) from the average value of the luminance value and the horizontal axis indicates the observation distance Dn.

In addition, in this embodiment, although a correction factor for the fluorescence-image preprocessing section 64 is illustrated as $x=1/\alpha$ and a correction factor for the reference-image preprocessing section 68 is illustrated as $y=1/\beta$, correction factors obtained by respectively multiplying x and y by a constant k may be used. Similar effects can also be achieved in this case.

In addition, if $\alpha$ or $\beta$ is chosen for the value of the constant k, it is possible to make the correction factor of either the fluorescence-image preprocessing section 64 or the reference-image preprocessing section 68 equal to unity, thereby reducing the amount of calculation.

This embodiment can be modified as follows.

Figure 11:
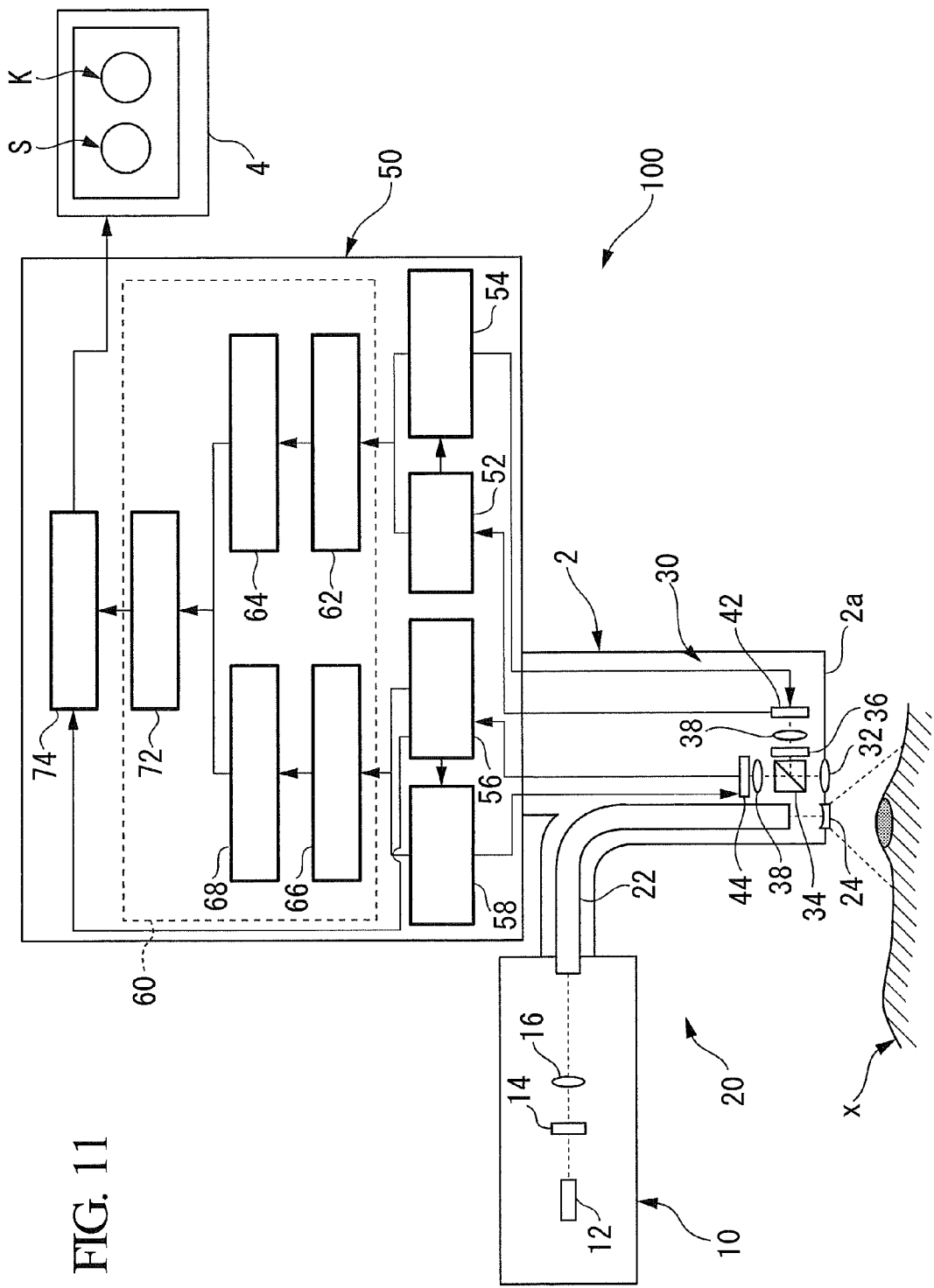
FIG. 11 is a block diagram showing, in outline, the configuration of a fluoroscopy apparatus according to a first modification of the first embodiment of the present invention.

For example, as a first modification, as shown in FIG. 11, the configuration may include the fluoroscopy apparatus 100 only and may omit the calibration device. In such a case, the preset correction factor x is stored in the fluorescence-image preprocessing section 64, and a preset correction factor y is stored in the reference-image preprocessing section 66.

Figure 12:
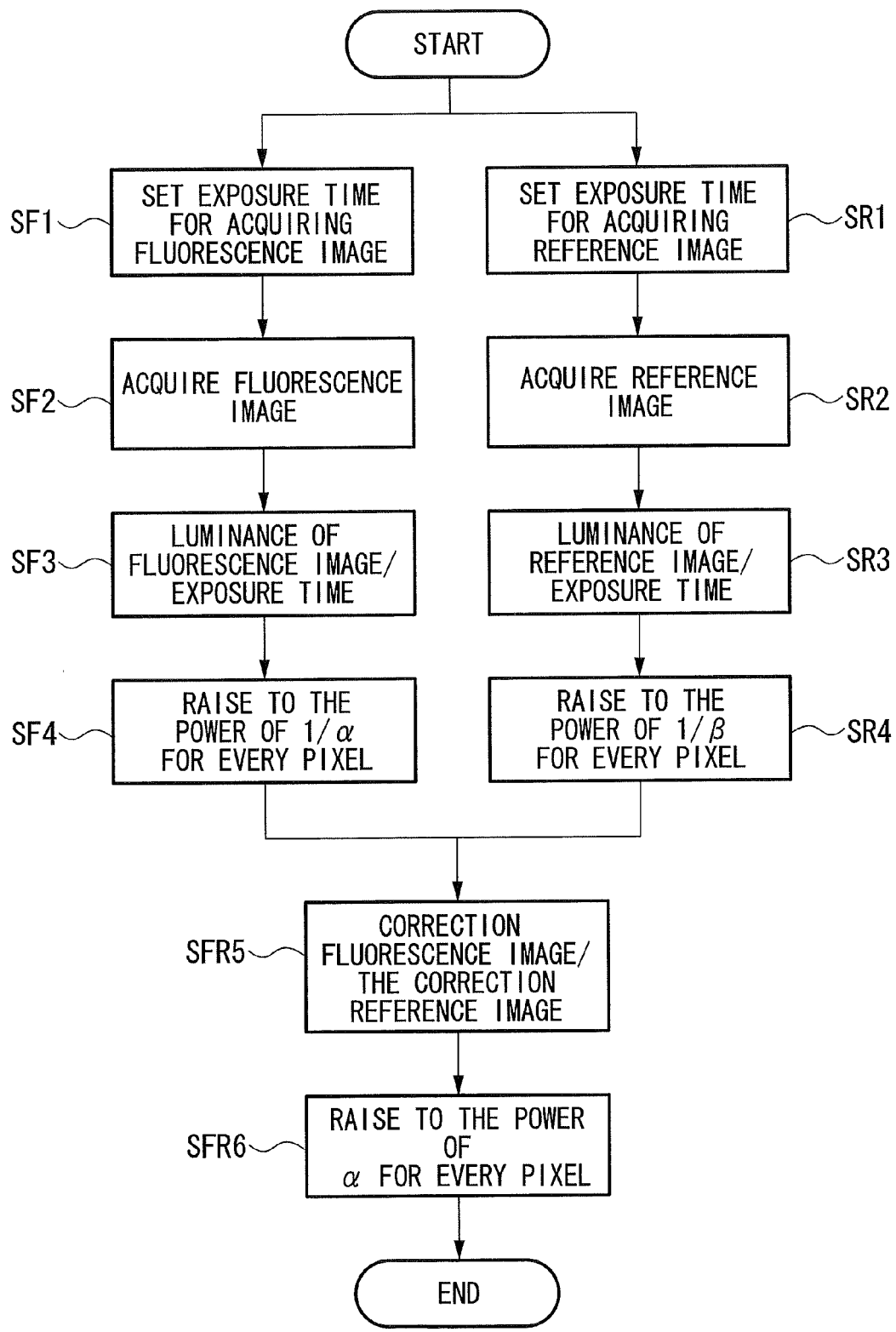
FIG. 12 is a flowchart of image processing in an image processing unit of a fluoroscopy apparatus according to a second modification of the first embodiment of the present invention.
Figure 13:
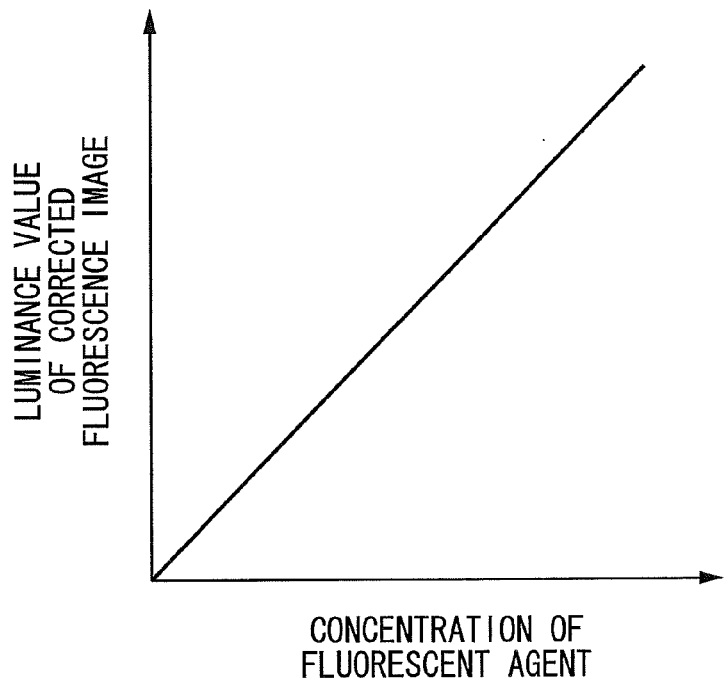
FIG. 13 is a graph showing the relationship between the luminance value in a fluoroscopy apparatus according to a second modification of the first embodiment of the present invention and the amount of fluorescent agent present.
Figure 14:
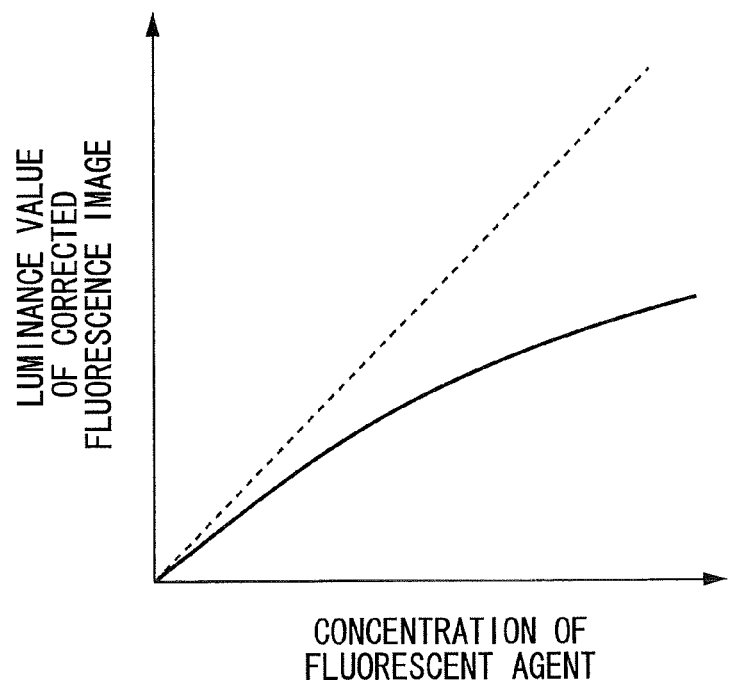
FIG. 14 is a graph showing the relationship between the luminance value, as a reference example, in the fluoroscopy apparatus in FIG. 13 and the amount of a fluorescent agent present.

In a second modification, for example, as shown in a flowchart in FIG. 12, in the image-correction unit 60, a postprocessing section (not shown) may be provided between the division processing unit 72 and the image-combining unit 74, and the postprocessing section may further raise the luminance value of each pixel in the corrected fluorescence image K obtained by the division processing unit 72 to the power of the first exponent $\alpha$ (step SFR6). By doing so, as shown in FIG. 13, it is possible to reduce the dependency on the distance by using the postprocessing section while maintaining the proportional relationship between the luminance value of the corrected fluorescence image K and the amount of fluorescent agent present (i.e., the concentration of fluorescent agent). As a reference example, FIG. 14 shows the relationship between the luminance value of the corrected fluorescence image K and the concentration of fluorescent agent when the luminance value is not raised to the power of the first exponent $\alpha$ by the postprocessing section.

In this embodiment, although the image-correction unit 60 is provided with the fluorescence-image preprocessing section 64, in a third modification, for example, the fluorescence-image preprocessing section 64 may be omitted, and the reference-image preprocessing section 68 may obtain the correction reference image by raising the luminance value of the reference image to the power of a third exponent $\alpha/\beta$ (or $\alpha/\beta$) that is obtained by dividing the first exponent $\alpha$ by the second exponent $\beta$.

Figure 15:
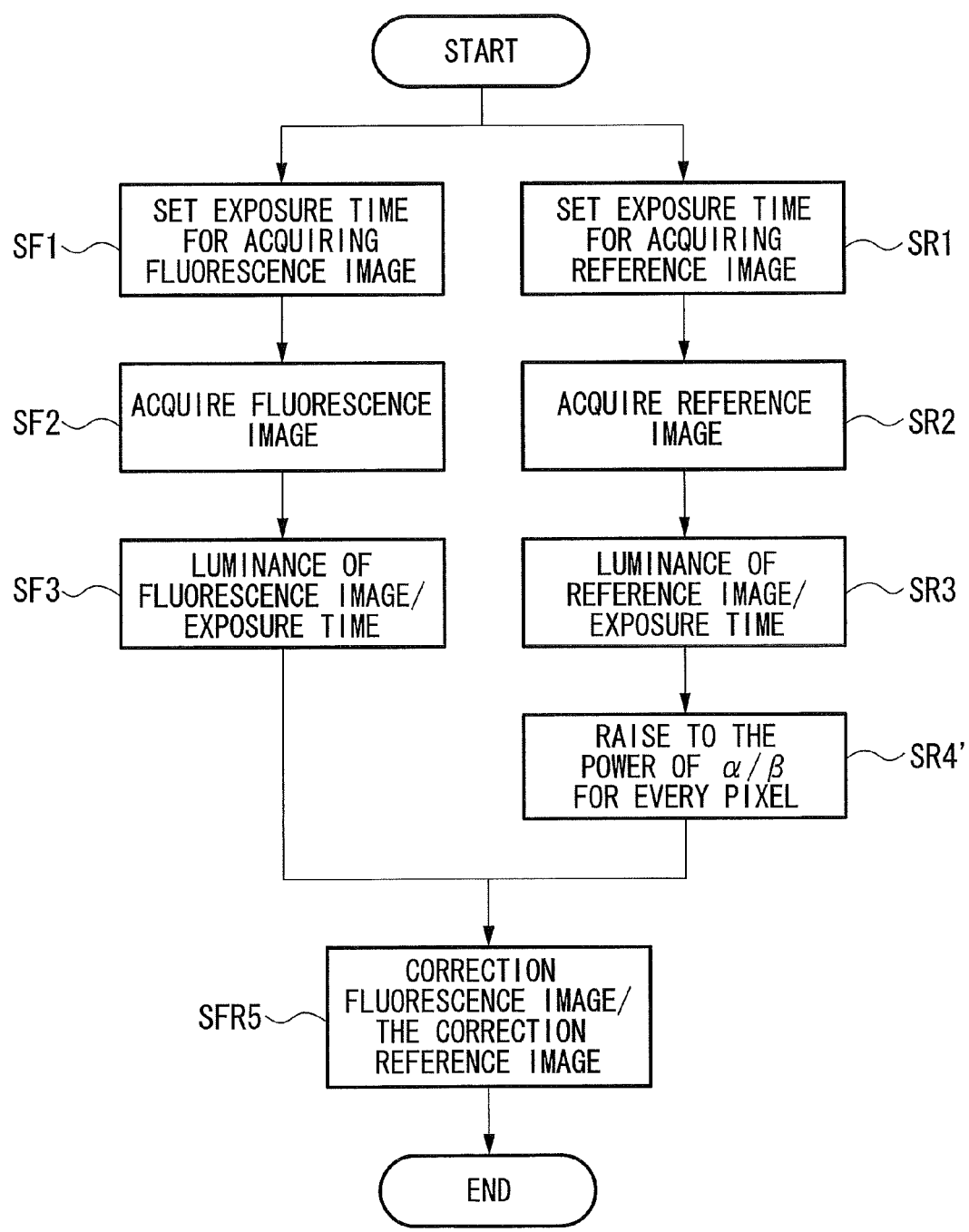
FIG. 15 is a flowchart of image processing in an image processing unit of a fluoroscopy apparatus according to a third modification of the first embodiment of the present invention.

In this case, as shown in a flowchart in FIG. 15, the fluorescence image normalized by the fluorescence-image normalization portion 62 may be sent to the division processing unit 72, and the power computation as described below may be performed by the reference-image preprocessing section 68 (step SR4'):

$$RL_{after} = B \times RL_{before}^{z} \quad (3)$$

Here, $RL_{after}$ is a luminance value of the correction reference image, $RL_{before}$ is a luminance value of the reference image, z is a third exponent ($a/\beta$ or $-\alpha\beta$), $\alpha$ is a first exponent, $\beta$ is a second exponent, and B is a constant.

By doing so, in the image-correction unit 60, it is sufficient to perform the power computation only once to correct the influence of the distance with high precision, and it is possible to obtain the corrected fluorescence image K in which the luminance value and the amount of the fluorescent agent present are in a directly proportional relationship.

In this embodiment, although the image-correction unit 60 is provided with the reference-image preprocessing section 66, in a fourth modification, for example, the reference-image preprocessing section 66 may be omitted, and the fluorescence-image preprocessing section 64 may obtain the correction fluorescence image by raising the luminance value of the fluorescence image to the power of a fourth exponent $\beta/\alpha$ (or $-\beta/\alpha$) that is obtained by dividing the second exponent $\beta$ by the first exponent $\alpha$, that is, the reciprocal of the third exponent $\alpha/\beta$ (or $-\alpha/\beta$).

In this case, the reference image normalized by the reference-image normalization portion 66 may be sent to the division processing unit 72, and the power computation as described below may be performed by the fluorescence-image preprocessing section 64:

$$FL_{after} = A \times FL_{before}^{z'} \quad (4)$$

Here, $FL_{after}$ is a luminance value of the correction fluorescence image, $FL_{before}$ is a luminance value of the fluorescence image, z' is a fourth exponent $\beta/\alpha$ (or $-\beta/\alpha$), $\alpha$ is a first exponent, $\beta$ is a second exponent, and A is a constant.

By doing so, in the image-correction unit 60, it is sufficient to perform the power computation only once to correct the influence of the distance with high precision.

In the third modification, although the reference-image preprocessing section 68 obtains the correction reference image by raising the luminance value of the reference image to the power of the third exponent $\alpha/\beta$ (or $-\alpha/\beta$), serving as the correction factor z, in a fifth modification, instead of the correction factor z, the correction factor (second correction factor) a, which is defined in the following method may be used in a dependency-constant determining unit (correction-factor calculating unit) (not shown).

As shown in FIG. 16, when two identical standard specimens 81 are positioned at different observation distances D0 and D1 within the range of the field of view of the fluorescence-imaging unit 42 and the white-light-imaging unit 44 and observed simultaneously, the correction factor a is set such that the luminance value obtained from the region of interest 85 of the corrected fluorescence image positioned at the observation distance D0 substantially matches the luminance value obtained from the region of interest 85 of the corrected fluorescence image positioned at the observation distance D1.

Specifically, the correction factor a that is obtained in the following arithmetic expression is calculated, in other words, the correction factor a is calculated such that the ratio of the fluorescence image to the correction reference image in which the luminance value of the reference image of the standard specimen 81 positioned at the observation distance D0 is raised to the power of the correction factor a substantially matches the ratio of the fluorescence image to the correction reference image in which the luminance value of the reference image of the standard specimen 81 positioned at the observation distance D1 is raised to the power of the correction factor a:

$$FL(D0)/RL(D0)^a = FL(D1)/RL(D1)^a \qquad (5)$$

$$a = \log(FL(D1)/FL(D0))/\log(RL(D1)/RL(D0)) \qquad (6)$$

Here, $FL(D0)$ is a luminance value of the fluorescence image at the observation distance D0, $RL(D0)$ is a luminance value of the reference image at the observation distance D0, $FL(D1)$ is a luminance value of the fluorescence image at the observation distance D1, and $RL(D1)$ is a luminance value of the reference image at the observation distance D1.

The reference-image preprocessing section 68 obtains the correction reference image of the observation target site X in a body cavity of a living body in accordance with the following arithmetic expression and sends it to the division processing unit 72:

$$RL_{after} = B \times RL_{before}^a \qquad (7)$$

According to expressions (5) and (6), the correction factor a is calculated such that the luminance values at two locations at different observation distances (D0 and D1) in the corrected fluorescence image K match each other. On the other hand, as shown in FIGS. 17(A) and 17(B), although the distance dependencies of the luminance value of the fluorescence image and of the luminance value of the reference image differ in the exponent, that is, the power of the distance, both are in a substantially inversely proportional relationship with respect to the power of the distance. Therefore, the values of the correction factor a decided at two locations that differ in the observation distances become close to the third exponent $\alpha/\beta$, and it is possible to reduce the difference in the distance dependencies even when correction using the correction factor a is performed on an image with an observation distance other than the observation distances D0 and D1.

If the observation distances D0 and D1 are close to each other, because the differences between the luminance values of the fluorescence images and the luminance values of the reference images at respective distances are small and errors tend to occur, it is preferred that the difference between the values of the observation distances D0 and D1 be as large as possible.

It is not required to obtain a plurality of images by changing the observation distance Dn to obtain exponents from power approximations, and even when the observation distances D0 and D1 are unknown, it is possible to calculate a correction factor a and to set the correction factor a easily.

In the fourth modification, although the fluorescence-image preprocessing section 64 obtains the correction fluorescence image by raising the luminance value of the fluorescence image to the power of the reciprocal of the third exponent $\beta/\alpha$ (or $-\beta/\alpha$), in a sixth modification, the correction may be performed using the reciprocal (first correction factor) 1/a of the correction factor a calculated in the fifth modification.

Specifically:

$$FL_{after} = A \times FL_{before}^{(1/a)} \qquad (8)$$

With this configuration, effects similar to those in the fifth modification can be achieved.

In the fourth modification, although the correction factor a is set as a correction value for the reference-image preprocessing section 64, such that the luminance values of the corrected fluorescence image in two identical standard specimens 81 at different observation distances Dn substantially match, in a seventh modification, correction factors (first correction factor and second correction factor) b and c obtained in accordance with the following arithmetic expressions may be set as the correction factors for the fluorescence-image preprocessing section 64 and the reference-image preprocessing section 68, respectively:

$$FL(D0)^b/RL(D0)^c = FL(D1)^b/RL(D1)^c \qquad (9)$$

$$c/b = \log(FL(D1)/FL(D0))/\log(RL(D1)/RL(D0)) \qquad (10)$$

In expression (10), although the ratio of b and c can be derived, numerical values cannot be decided. Thus, the value of c can be decided in accordance with expression (10) by arbitrarily setting the value of b (for example 2). Instead of this, after the value of c is set arbitrarily, the value of b may be decided in accordance with expression (10).

The decided correction factor b is set in the fluorescence-image preprocessing section 64, and the fluorescence-image preprocessing section 64 performs the following computation:

$$FL_{after} = A \times FL_{before}^b \qquad (11)$$

The decided correction factor c is set in the reference-image preprocessing section 68, and the reference-image preprocessing section 68 performs the following computation:

$$RL_{after} = B \times RL_{before}^c \qquad (12)$$

The value obtained by dividing the correction factor c by the correction factor b is equal to the correction factor a calculated in the fourth modification, and it also has a value close to that of the third exponent $\alpha/\beta$. This modification also achieves effects equivalent to those in the fourth modification.

Figure 18:
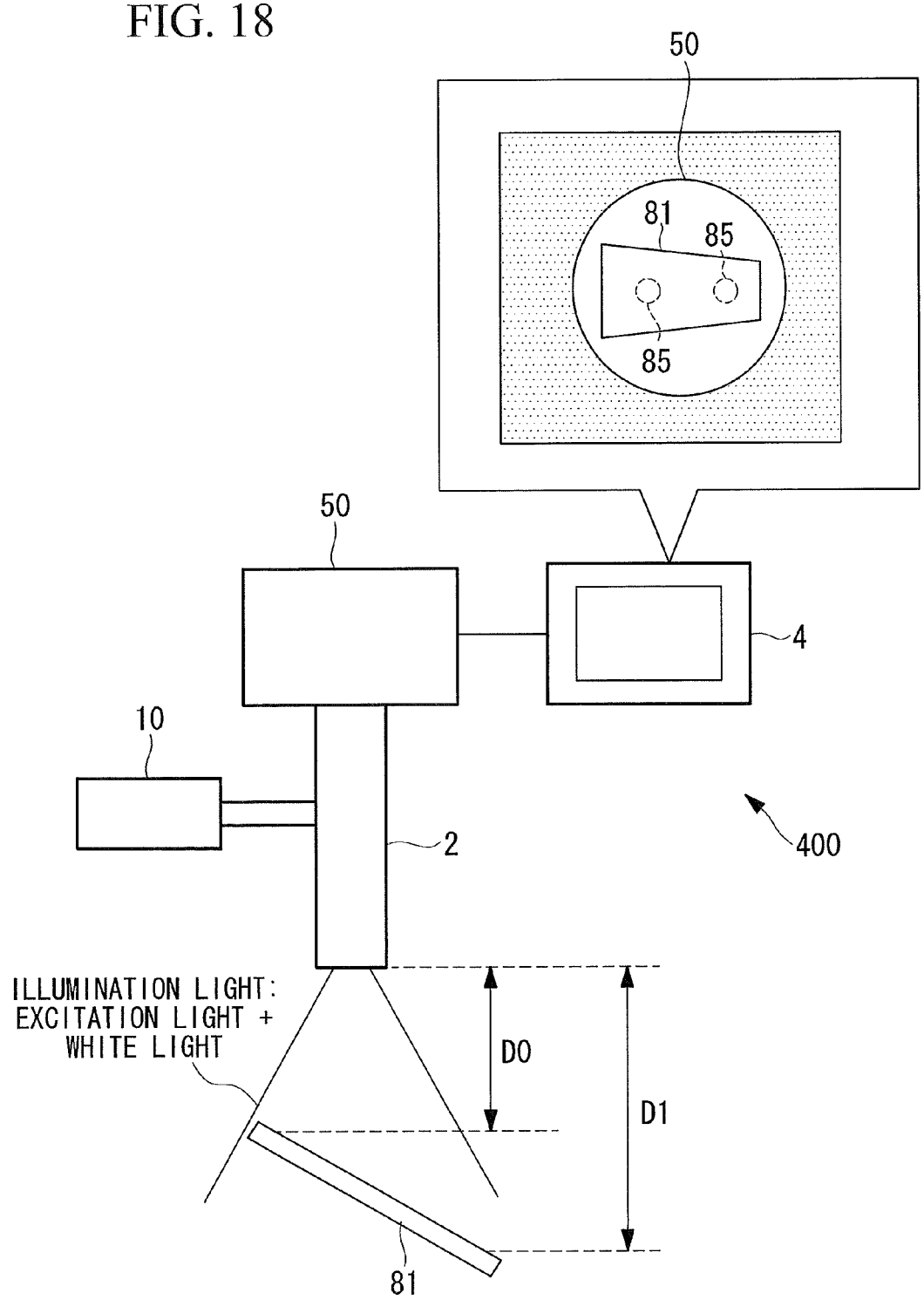
FIG. 18 is a diagram showing a state in which simultaneous observation of two regions of interest in a standard specimen at different observation distances is performed with a fluoroscopy apparatus according to an eighth modification of the first embodiment of the present invention.

In the fifth to seventh modifications, although two identical standard specimens 81 are positioned at different observation distances D0 and D1, and the correction factors a are calculated from the luminance values obtained from the respective regions of interest 85, in an eighth modification, as shown in FIG. 18, the standard specimen 81 may be placed at an angle within the ranges of the fields of view of the fluorescence-imaging unit 42 and the white-light-imaging unit 44, and the correction factors a may be calculated from the luminance values obtained from two regions of interest 85 located at different observation distances Dn on one standard specimen 81.

In this case, as in this embodiment, the correction factor a, and the correction factors b and c may be calculated such that the luminance value obtained in the region of interest 85 in the corrected fluorescence image at the observation distance D0 substantially matches the luminance value obtained in the region of interest 85 in the corrected fluorescence image at the observation distance D1. By doing so, it is possible to set the correction factors a, b, and c easily by using only one standard specimen 81.

Figure 19:
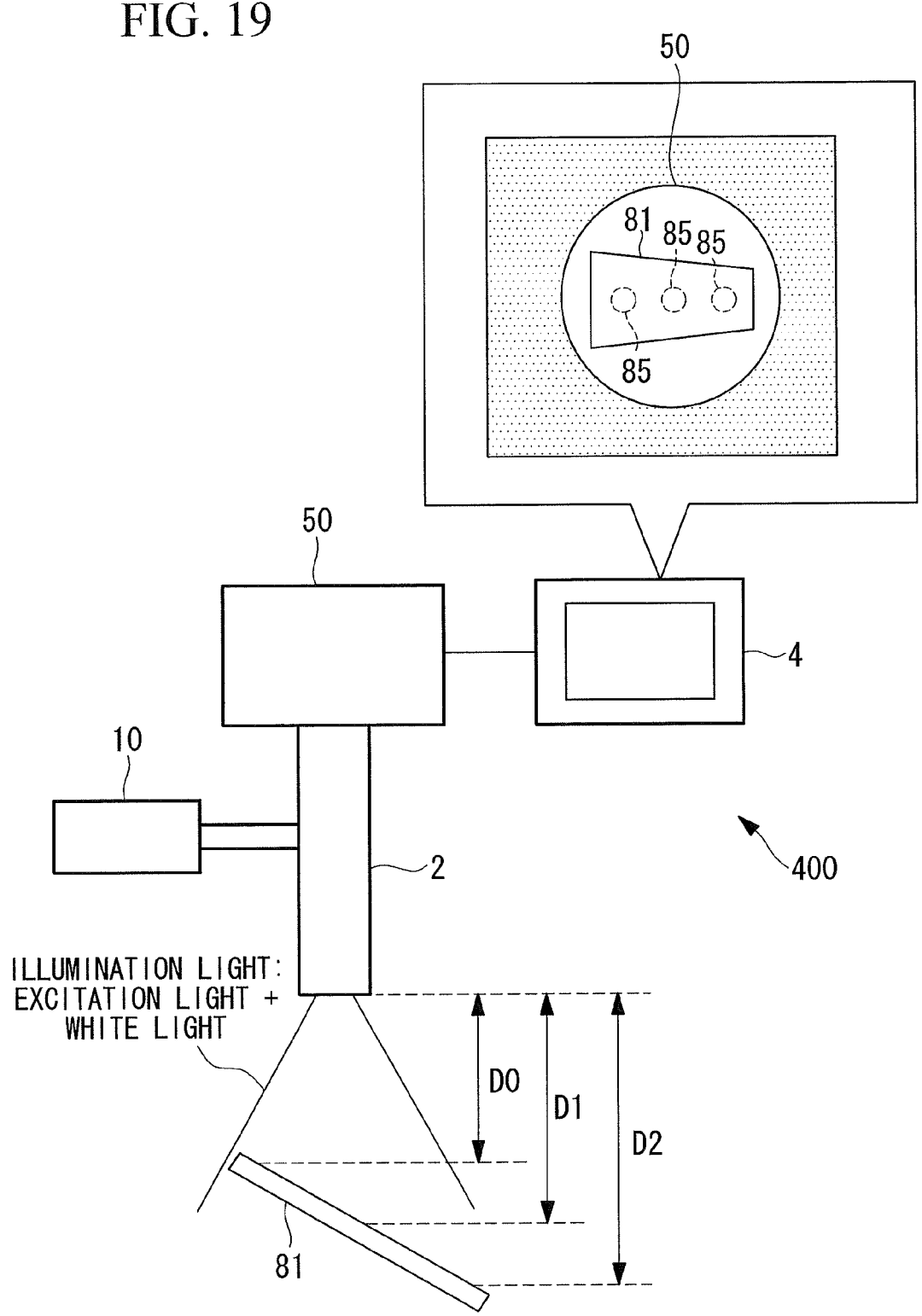
FIG. 19 is a diagram showing a state in which simultaneous observation of three or more regions of interest in a standard specimen at different observation distances is performed with a fluoroscopy apparatus according to a ninth modification of the first embodiment of the present invention.

In the fifth modification, although the correction factor a is set by the luminance values obtained from two regions of interest 85 located at different observation distances Dn, in a ninth modification, as shown in FIG. 19, the correction factor a may be calculated from the luminance values of two regions of interest 85 having observation distances Dn that are close to each other among the luminance values obtained from three or more regions of interest 85 in the standard specimen 81 placed at an angle within the ranges of the fields of view of the fluorescence-imaging unit 42 and the white-light-imaging unit 44.

For example, a correction factor a01 in which the luminance value obtained from the region of interest 85 at the observation distance D0 substantially matches the luminance value obtained from the region of interest 85 at the observation distance D1 and a correction factor a02 in which the luminance value obtained from the region of interest 85 at the observation distance D1 substantially matches the luminance value obtained from the region of interest 85 at the observation distance D2 may be calculated, and the correction factor a may be derived from the average values (a=(a01+a02)/2) of each of the correction factors a01 and a02. By doing so, it is possible to reduce the errors caused in the correction factors a on the basis of the luminance values of a plurality of regions of interest 85.

Figure 20:
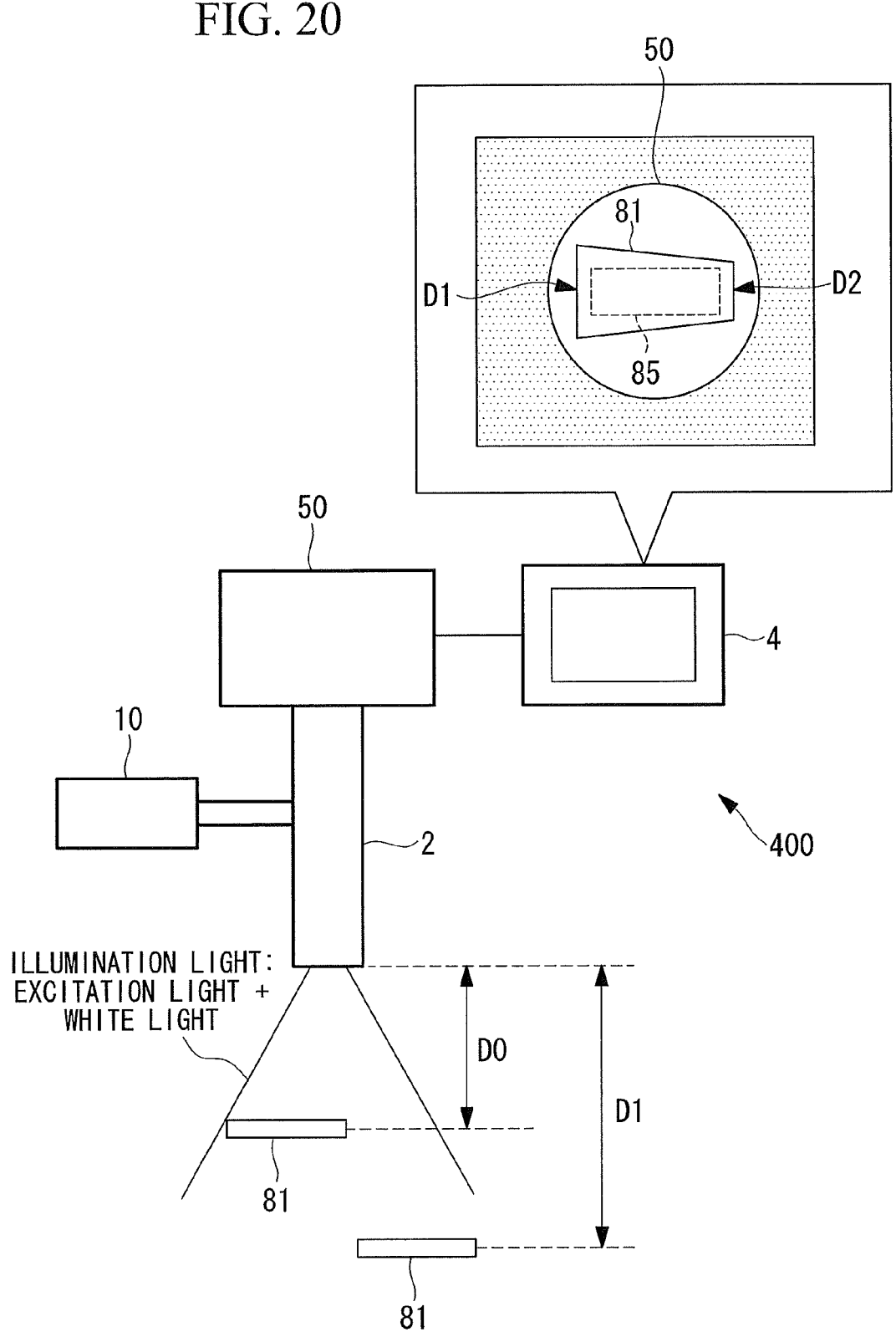
FIG. 20 is a diagram showing a state in which simultaneous observation of regions of interest, including a continuous change in distance, in a standard specimen is performed with a fluoroscopy apparatus according to a tenth modification of the first embodiment of the present invention.

In a tenth modification, as shown in FIG. 20, with the standard specimen 81 placed at an angle within the ranges of the fields of view of the fluorescence-imaging unit 42 and the white-light-imaging unit 44, a region including a continuous distance change, for example, from the observation distance D0 to the observation distance D1, may be set as the region of interest 85, the correction factor a may be varied from 1 in increments of 0.05 to calculate $FL/RL^a$ for every pixel in the region of interest 85, and, as shown in FIG. 21, the standard deviation σ of $FL/RL^a$ in the region of interest 85 for every correction factor a may be calculated, and thereby, the correction factor a that yields the smallest standard deviation σ may be set. By doing so, the errors caused in the correction factor a can be reduced.

Second Embodiment

Next, a fluoroscopy apparatus and fluorescence-image processing method according to a second embodiment of the present invention will be described.

Figure 22:
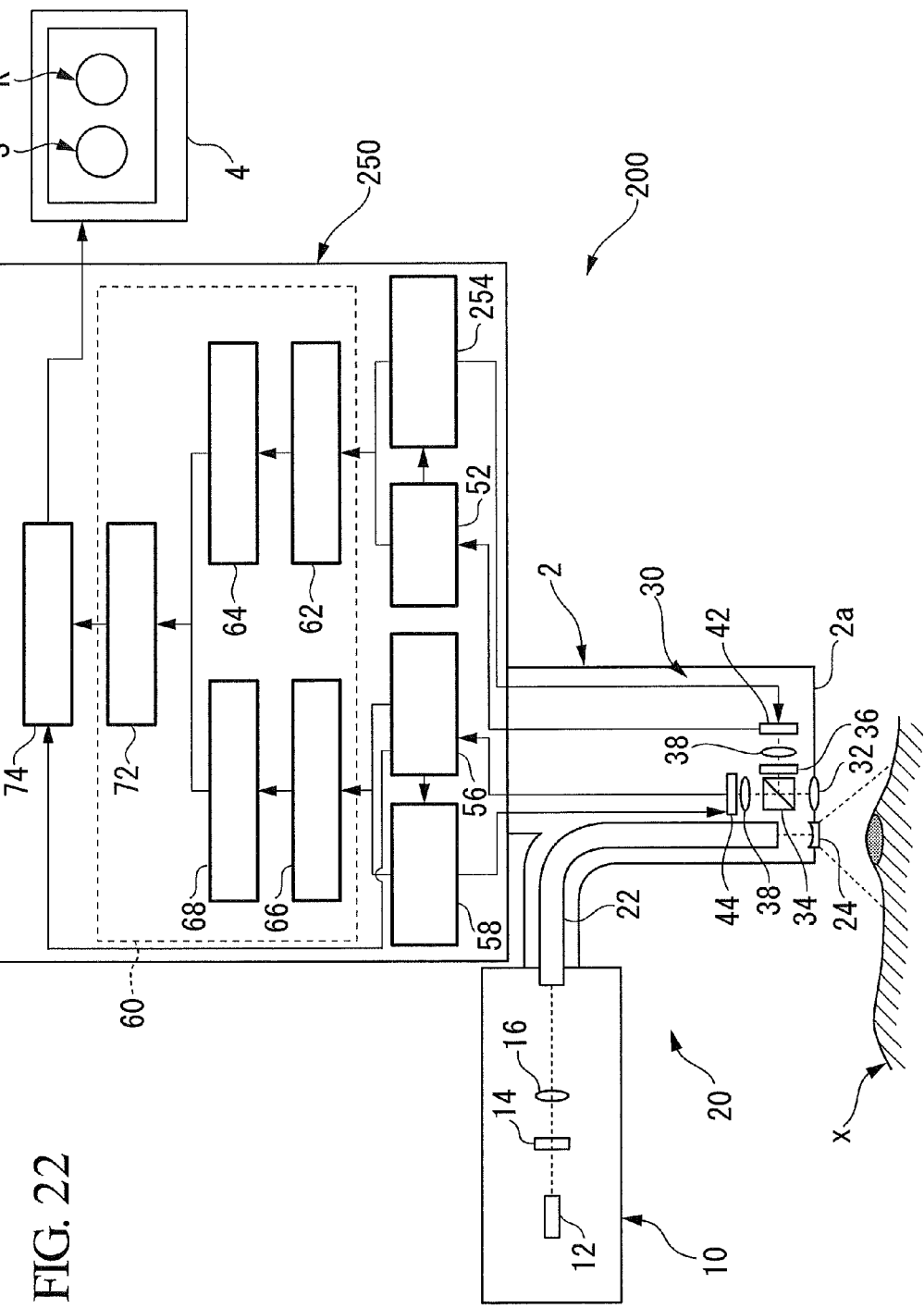
FIG. 22 is a block diagram showing, in outline, the configuration of a fluoroscopy apparatus according to a second embodiment of the present invention.

The fluoroscopy apparatus 200 according to this embodiment differs from the first embodiment in that, as shown in FIG. 22, the image processing unit 250 is provided with, instead of the fluorescence exposure-time adjusting portion 54, a fluorescence-gain-value adjusting portion (image-acquisition condition adjusting portion) 254 that adjusts a gain value (image acquisition condition, gain factor) that amplifies the fluorescence image information acquired by the fluorescence-imaging unit 42.

In the following, parts having the same configuration as those in the fluoroscopy apparatuses 100 and 101 according to the first embodiment will be assigned the same reference signs, and a description thereof will be omitted.

The fluorescence-gain-value adjusting portion 254 adjusts the gain value of the fluorescence-imaging unit 42 on the basis of the luminance value of the fluorescence image generated by the fluorescence-image generating unit 52.

Figure 23:
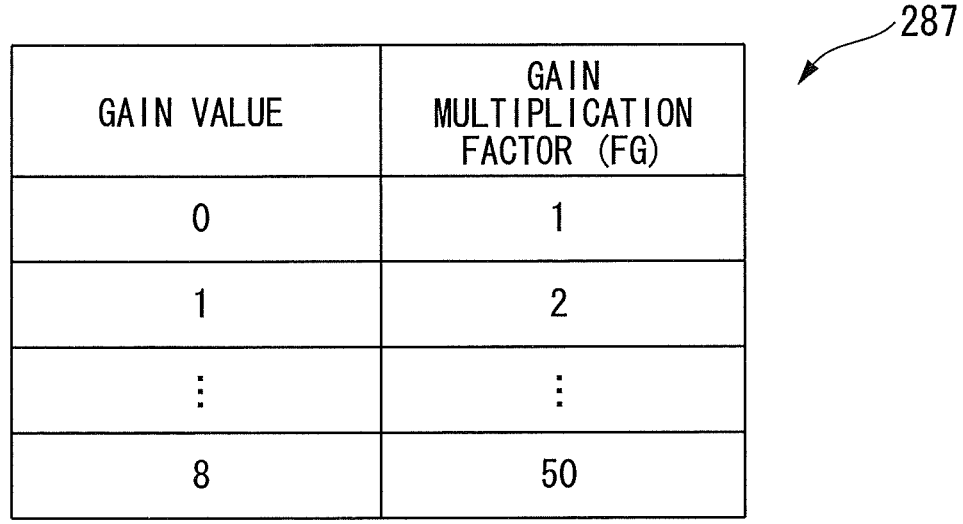
FIG. 23 is a diagram showing an example of a gain conversion table provided in a fluorescence-image normalization portion of the fluoroscopy apparatus in FIG. 22.

The gain value of the fluorescence-imaging unit 42 that is set by the fluorescence-gain-value adjusting portion 254 is input to the fluorescence-image normalization portion 62. In addition, the fluorescence-image normalization portion 62 is provided with a gain-factor conversion table 287, like that shown in FIG. 23, in which gain values and gain multiplication factors are associated with each other.

Figure 24:
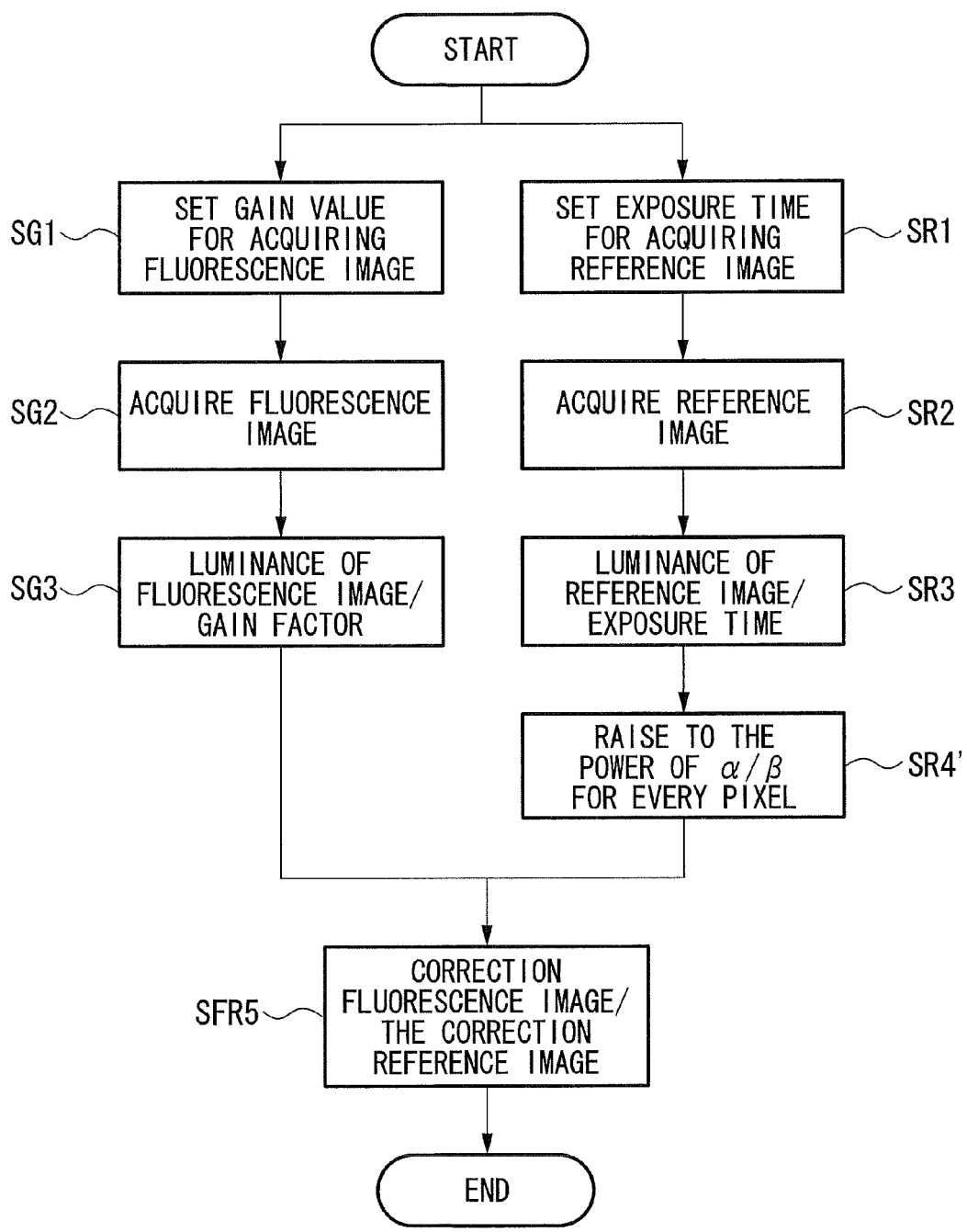
FIG. 24 is a flowchart of image processing in the image processing unit in FIG. 22.

With the thus-configured fluoroscopy apparatus 200, as shown in a flowchart in FIG. 24, the gain value of the fluorescence-imaging unit 42 is set by the fluorescence-gain-value adjusting portion 254 on the basis of the luminance value of the fluorescence image generated by the fluorescence-image generating unit 52 (step SG1). By doing so, a fluorescence image having suitable brightness is obtained by the fluorescence-image generating unit 52 regardless of the incident light intensity of the fluorescence generated at the observation target site X (step SG2).

In the fluorescence-image normalization portion 62, the luminance value of the fluorescence image read out from the fluorescence-image generating unit 52 is divided by the gain multiplication factor that corresponds to the gain value at the time of acquisition of the fluorescence image by the fluorescence-imaging unit 42 (step SG3). By doing so, the influence of the gain value in the fluorescence image is normalized, and the fluorescence image can be standardized at a certain luminance value per multiplication value.

Third Embodiment

Next, a fluoroscopy apparatus and a fluorescence-image processing method according to a third embodiment of the present invention will be described.

Figure 25:
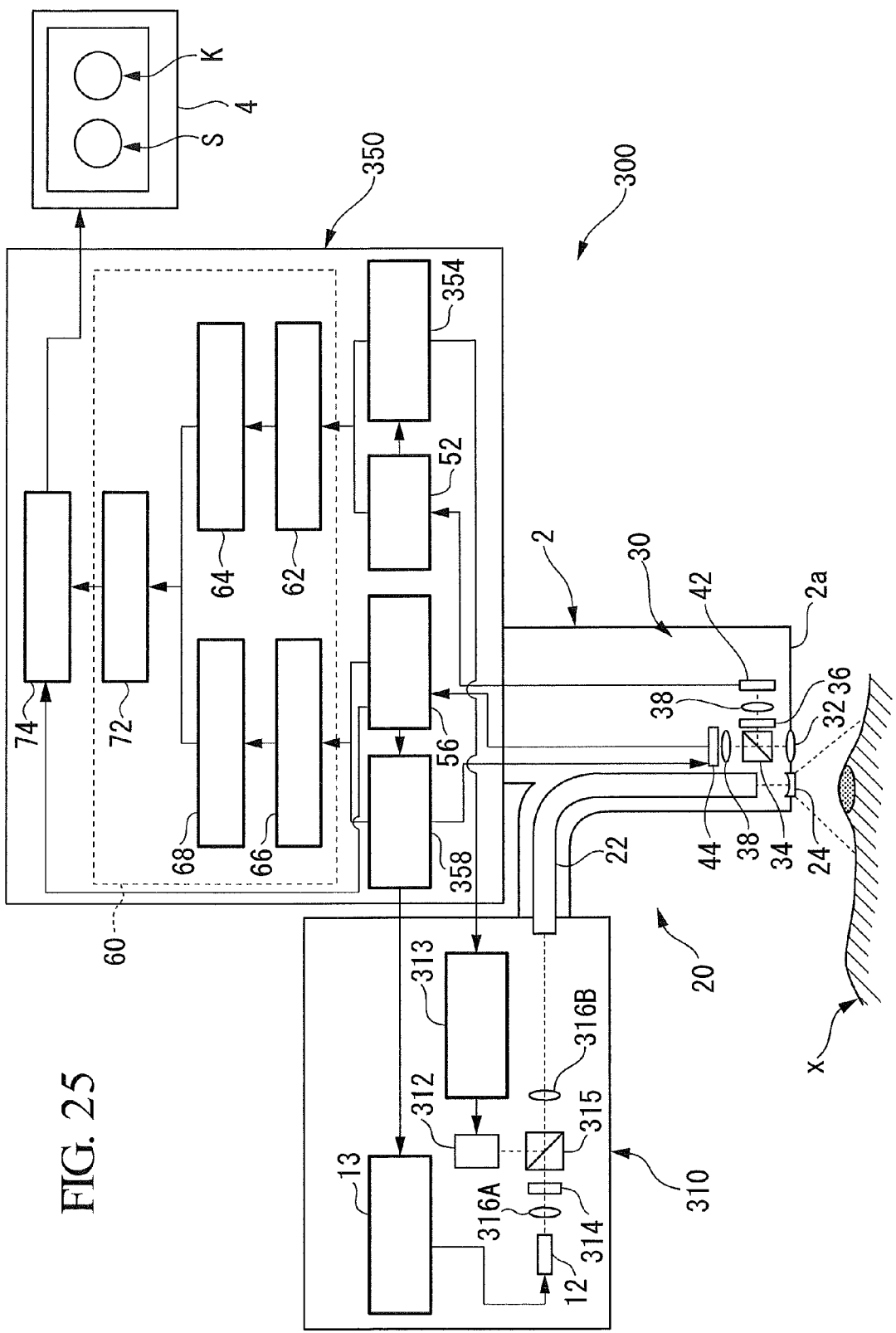
FIG. 25 is a block diagram showing, in outline, the configuration of a fluoroscopy apparatus according to a third embodiment of the present invention.

The fluoroscopy apparatus 300 according to this embodiment differs from the first embodiment in that, as shown in FIG. 25, the light source 310 is further provided with a semiconductor laser 312, and the image processing unit 350 is provided with, instead of the fluorescence exposure-time adjusting portion 54 and the white-light exposure-time adjusting unit 58, an excitation-light adjusting portion (image-acquisition condition adjusting portion) 354 that adjusts the light-adjustment level of the excitation light emitted from the illumination unit 20 and a white-light adjusting portion (image-acquisition condition adjusting portion) 358 that adjusts the light-adjustment level of the illumination light.

In the following, parts having the same configuration as those in the fluoroscopy apparatuses 100 and 101 according to the first embodiment will be assigned the same reference signs, and a description thereof will be omitted.

The light source 310 is provided with the xenon lamp 12, a xenon lamp controller 13, an infrared-cut filter 314 that blocks infrared light in the illumination light and transmits only the white light emitted from the xenon lamp 12, the semiconductor laser 312 that emits the excitation light in the wavelength band of 740 nm, a semiconductor laser controller 313, and a light source dichroic mirror 315 that transmits the white light transmitted through the infrared-cut filter 314 and that reflects the excitation light emitted from the semiconductor laser 312, thereby guiding the white light and the excitation light into the same optical path. The infrared-cut filter 314 transmits only, for example, the white light in the wavelength band between 400 and 680 nm. Reference sign 316A is a first coupling lens that focuses the white light transmitted through the infrared-cut filter 314, and reference sign 316B is a second coupling lens that focuses the white light and the excitation light that are guided into the same optical path by the light-source dichroic mirror 315.

The excitation-light adjusting portion 354 adjusts the light-adjustment level of the semiconductor laser 312 with the semiconductor laser controller 313 on the basis of the luminance value of the fluorescence image generated by the fluorescence-image generating unit 52.

Similarly, the white-light adjusting portion 358 adjusts the light-adjustment level of the xenon lamp 12 with the xenon lamp controller 13 on the basis of the luminance value of the reference image generated by the reference-image generating unit 56.

Figure 26:
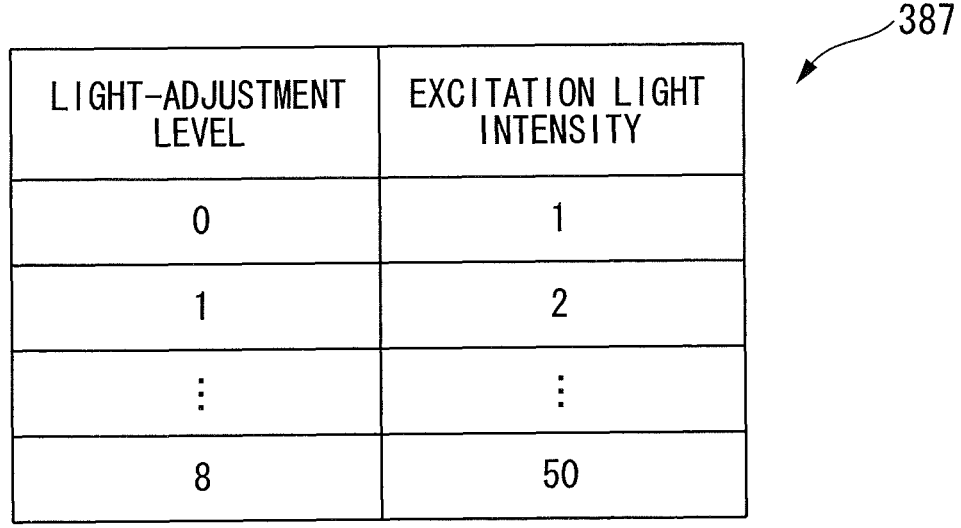
FIG. 26 is a diagram showing an example of an excitation-light intensity conversion table provided in a fluorescence-image normalization portion of the fluoroscopy apparatus in FIG. 25.

The light-adjustment level of the semiconductor laser controller 313 that is set by the excitation-light adjusting portion 354 is input to the fluorescence-image normalization portion 62. The fluorescence-image normalization portion 62 is provided with an excitation-light intensity conversion table 387, like that shown in FIG. 26, in which the light-adjustment level and the excitation-light intensity are associated with each other.

Similarly, the light-adjustment level of the xenon lamp controller 13 that is set by the white-light adjusting portion 358 is input to the reference-image normalization portion 66. The reference-image normalization portion 66 is provided with a white-light intensity conversion table (not shown) in which the light-adjustment level and the white-light intensity (illumination light intensity) are associated with each other. The excitation-light intensity and the white-light intensity may be decided by respective intensity ratios based on the minimum values.

With the thus-configured fluoroscopy apparatus 300, the white light emitted from the xenon lamp 12, transmitted through the infrared-cut filter 314, and focused by the first coupling lens 316A is transmitted through the light source dichroic mirror 315, and the excitation light emitted from the semiconductor laser 312 is reflected at the light source dichroic mirror 315, and both the white light and the excitation light are guided along the same optical path and are focused by a second coupling lens 316B so as to enter the light guide fiber 22.

Figure 27:
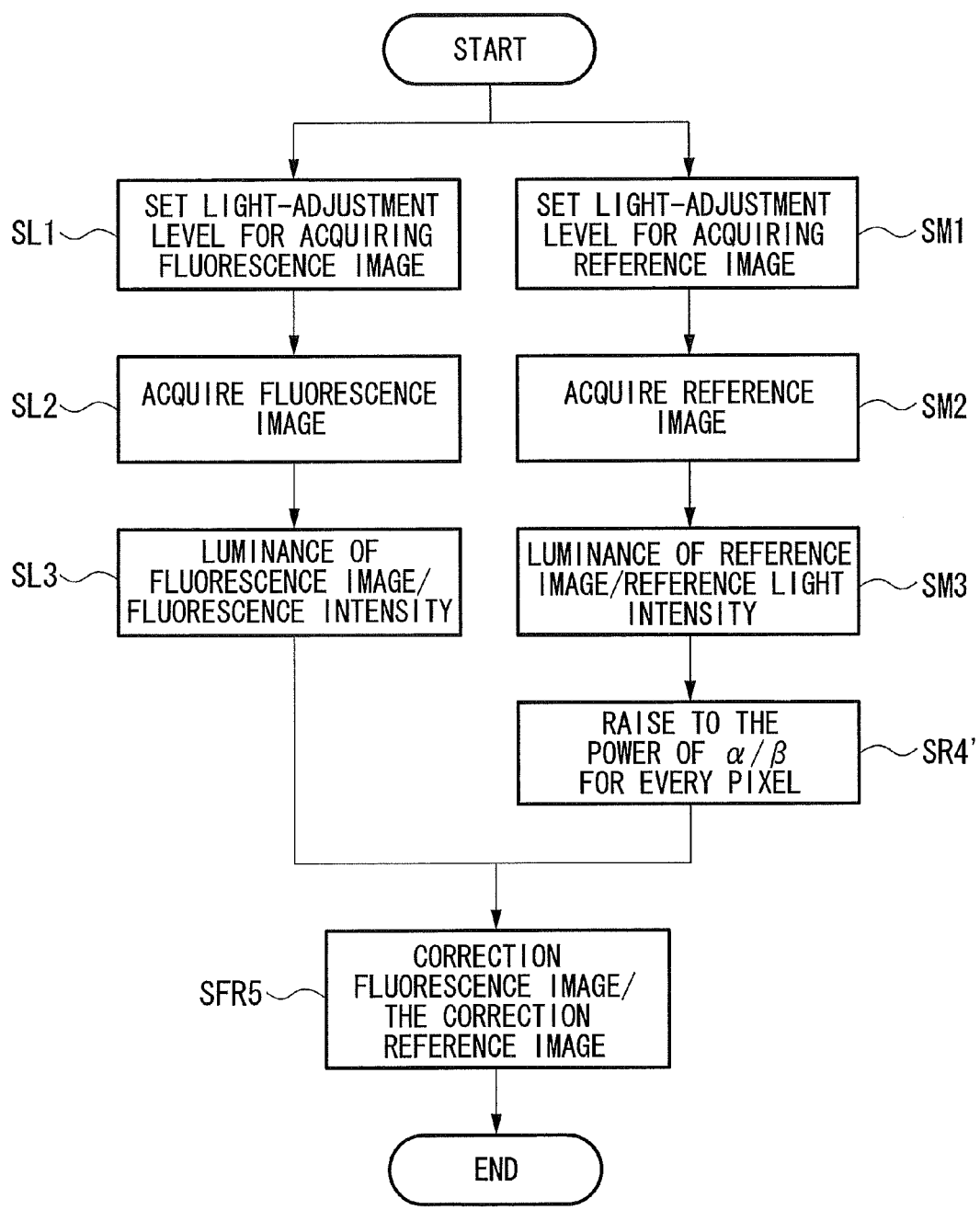
FIG. 27 is a flowchart of image processing in the image processing unit in FIG. 25.

In the image-correction unit 60, as shown in a flowchart in FIG. 27, the light-adjustment level of the semiconductor laser controller 313 is set by the excitation-light adjusting portion 354 on the basis of the luminance value of the fluorescence image generated by the fluorescence-image generating unit 52 (step SL1). By doing so, in the fluorescence-image generating unit 52, a fluorescence image having suitable brightness is obtained by varying the intensity of the fluorescence generated at the observation target site X (step SL2).

Similarly, the light-adjustment level of the xenon lamp controller 13 is set by the white-light adjusting portion 358 on the basis of the luminance value of the reference image generated by the reference-image generating unit 56 (step SM1). By doing so, in the reference-image generating unit 56, a reference image having suitable brightness is obtained by varying the intensity of the white light returning from the observation target site X (step SM2).

Then, the fluorescence-image normalization portion 62 performs division of the luminance value of the fluorescence image read out from the fluorescence-image generating unit 52 by the excitation-light intensity corresponding to the light-adjustment level of the semiconductor laser controller 313 (step SL3). By doing so, the influence of the light-adjustment level of the excitation light is normalized, and the fluorescence image can be standardized at a certain luminance value per unit of excitation-light intensity.

In addition, the reference-image normalization portion 66 divides the luminance value of the reference image read out from the reference-image generating unit 56 by the white-light intensity corresponding to the light-adjustment level of the xenon lamp controller 13 (step SM3). By doing so, the influence of the light-adjustment level of the illumination light is normalized, and the reference image can be standardized at a certain luminance value per unit of white-light intensity.

Although the embodiments of the present invention have been described above with reference to the drawings, the specific configurations are not limited to these embodiments, and design alterations and the like within a range that does not depart from the spirit of the present invention are encompassed. For example, the present invention is not limited to aspects that are employed in the above-described embodiments and modifications thereof; without particular limitation, it may also be applied to embodiments formed by appropriately combining these embodiments and modifications thereof.

In addition, each of the above-mentioned embodiments has been described in terms of examples where near-infrared fluorescence and white light are used. However, the present invention is not limited thereto and, for example, fluorescence having visible wavelengths may be used in place of the near-infrared fluorescence, or excitation light having visible wavelengths may be used in place of the white light. In addition, for example, in the fluorescence-image preprocessing section 64 and the reference-image preprocessing section 68, the power computation may be performed after noise components in the fluorescence-imaging unit 42 and the white-light-imaging unit 44 have been subtracted. By doing so, the precision of the power computation can be improved.

REFERENCE SIGNS LIST 10, 310 light source
20 illumination unit (illumination portion)
42 fluorescence-imaging unit
44 white-light-imaging unit (return-light imaging unit)
54 fluorescence exposure-time adjusting portion (image-acquisition condition adjusting portion)
58 white-light exposure-time adjusting unit (image-acquisition condition adjusting portion)
60, 460 image-correction unit
92 translation stage (observation-state setting mechanism)
98 dependency-constant determining unit (exponent calculating unit, correction-factor calculating unit)
100, 101, 200, 300, 400 fluoroscopy apparatus
102 calibration device
150 fluoroscopy system
254 fluorescence-gain-value adjusting portion (image-acquisition condition adjusting portion)
354 excitation-light adjusting portion (image-acquisition condition adjusting portion)
358 white-light adjusting portion (image-acquisition condition adjusting portion)

What is claimed is:
1. A fluoroscopy apparatus comprising:
an illumination portion having a light source that radiates illumination light and excitation light onto a subject;
a fluorescence-imaging unit that acquires a fluorescence image by imaging fluorescence generated at the subject by the radiation of the excitation light from the illumination portion;

a return-light imaging unit that acquires a reference image by imaging return light returning from the subject by the radiation of the illumination light from the illumination portion; and an image-correction unit that corrects the fluorescence image acquired by the fluorescence-imaging unit by using the reference image acquired by the return-light imaging unit, wherein in the image-correction unit, a correction fluorescence image is obtained by raising a luminance value of the fluorescence image to the power of the reciprocal of a first exponent that is obtained by a power approximation of a characteristic of luminance versus distance from the illumination portion to the subject, for the fluorescence image acquired by the fluorescence-imaging unit when the excitation light of a prescribed intensity is radiated towards the subject; a correction reference image is obtained by raising a luminance value of the reference image to the power of the reciprocal of a second exponent that is obtained by a power approximation of a characteristic of luminance versus distance from the illumination portion to the subject, for the reference image obtained by the return-light imaging unit when the illumination light of a prescribed intensity is radiated towards the subject; and a corrected fluorescence image is obtained by dividing the correction fluorescence image by the correction reference image.

2. A fluoroscopy apparatus according to claim 1, wherein the image-correction unit further raises the luminance value of the corrected fluorescence image to the power of the first exponent.

3. A fluoroscopy apparatus according to claim 1, further comprising an image-acquisition condition adjusting portion that adjusts an image acquisition condition on the basis of the luminance value of the fluorescence image acquired by the fluorescence-imaging unit, wherein the image-correction unit normalizes the luminance of the fluorescence image by the image acquisition condition.

4. A fluoroscopy apparatus according to claim 3, wherein the image-acquisition condition adjusting portion adjusts an exposure time of the fluorescence-imaging unit, and the image-correction unit divides the luminance value of the fluorescence image by the exposure time.

5. A fluoroscopy apparatus according to claim 3, wherein the image-acquisition condition adjusting portion adjusts a gain factor of the fluorescence-imaging unit, and the image-correction unit divides the luminance value of the fluorescence image by the gain factor.

6. A fluoroscopy apparatus according to claim 3, wherein the image-acquisition condition adjusting portion adjusts excitation-light intensity from the illumination portion, and the image-correction unit divides the luminance value of the fluorescence image by the excitation-light intensity.

7. A fluoroscopy apparatus according to claim 1, further comprising an image-acquisition condition adjusting portion that adjusts the image acquisition condition on the basis of the luminance value of the reference image acquired by the return-light imaging unit, wherein the image-correction unit normalizes the luminance of the reference image by the image acquisition condition.

8. A fluoroscopy apparatus according to claim 7, wherein the image-acquisition condition adjusting portion adjusts an exposure time of the return-light imaging unit, and the image-correction unit divides the luminance value of the reference image by the exposure time.

9. A fluoroscopy apparatus according to claim 7, wherein the image-acquisition condition adjusting portion adjusts a gain factor of the return-light imaging unit, and the image-correction unit divides the luminance value of the reference image by the gain factor.

10. A fluoroscopy apparatus according to claim 7, wherein the image-acquisition condition adjusting portion adjusts illumination light intensity from the illumination portion, and the image-correction unit divides the luminance value of the reference image by the illumination light intensity.

11. A fluoroscopy system comprising a fluoroscopy apparatus according to claim 1 and a calibration device that calibrates the fluoroscopy apparatus, wherein the calibration device is provided with a standard specimen and an observation-state setting mechanism that changeably sets an observation distance of the fluoroscopy apparatus relative to the standard specimen, and wherein the fluoroscopy apparatus or the calibration device is provided with an exponent calculating unit that calculates the first exponent and the second exponent on the basis of the observation distance set by the observation-state setting mechanism and the fluorescence image and the reference image acquired by imaging the standard specimen with the fluoroscopy apparatus.

12. A fluoroscopy apparatus according to claim 2, further comprising an image-acquisition condition adjusting portion that adjusts an image acquisition condition on the basis of the luminance value of the fluorescence image acquired by the fluorescence-imaging unit, wherein the image-correction unit normalizes the luminance of the fluorescence image by the image acquisition condition.

13. A fluoroscopy apparatus according to claim 2, further comprising an image-acquisition condition adjusting portion that adjusts the image acquisition condition on the basis of the luminance value of the reference image acquired by the return-light imaging unit, wherein the image-correction unit normalizes the luminance of the reference image by the image acquisition condition.

14. A fluoroscopy system comprising a fluoroscopy apparatus according to claim 2 and a calibration device that calibrates the fluoroscopy apparatus, wherein the calibration device is provided with a standard specimen and an observation-state setting mechanism that changeably sets an observation distance of the fluoroscopy apparatus relative to the standard specimen, and wherein the fluoroscopy apparatus or the calibration device is provided with an exponent calculating unit that calculates the first exponent and the second exponent on the basis of the observation distance set by the observation-state setting mechanism and the fluorescence image and the reference image acquired by imaging the standard specimen with the fluoroscopy apparatus.

15. A fluoroscopy apparatus according to claim 12, wherein the image-acquisition condition adjusting portion adjusts an exposure time of the fluorescence-imaging unit, and the image-correction unit divides the luminance value of the fluorescence image by the exposure time.

16. A fluoroscopy apparatus according to claim 12, wherein the image-acquisition condition adjusting portion adjusts a gain factor of the fluorescence-imaging unit, and the image-correction unit divides the luminance value of the fluorescence image by the gain factor.

17. A fluoroscopy apparatus according to claim 12, wherein the image-acquisition condition adjusting portion adjusts excitation-light intensity from the illumination portion, and the image-correction unit divides the luminance value of the fluorescence image by the excitation-light intensity.

18. A fluoroscopy apparatus according to claim 13, wherein the image-acquisition condition adjusting portion adjusts an exposure time of the return-light imaging unit, and
the image-correction unit divides the luminance value of the reference image by the exposure time.

19. A fluoroscopy apparatus according to claim 13, wherein the image-acquisition condition adjusting portion adjusts a gain factor of the return-light imaging unit, and
the image-correction unit divides the luminance value of the reference image by the gain factor.

20. A fluoroscopy apparatus according to claim 13, wherein the image-acquisition condition adjusting portion adjusts illumination light intensity from the illumination portion, and
the image-correction unit divides the luminance value of the reference image by the illumination light intensity.

\* \* \* \* \*